(12) United States Patent
Shawver et al.

(10) Patent No.: US 8,216,290 B2
(45) Date of Patent: Jul. 10, 2012

(54) AUTOMATED TEMPERATURE CONTRAST AND DYNAMIC PRESSURE MODULES FOR A HOT OR COLD WRAP THERAPY SYSTEM

(75) Inventors: Michael Shawver, Mill Valley, CA (US); Howard Edelman, San Francisco, CA (US)

(73) Assignee: VitalWear, Inc., South San Francisco, CA (US)

( * ) Notice: Subject to any disclaimer, the term of this patent is extended or adjusted under 35 U.S.C. 154(b) by 575 days.

(21) Appl. No.: 12/420,055

(22) Filed: Apr. 8, 2009

(65) Prior Publication Data
US 2009/0254160 A1    Oct. 8, 2009

Related U.S. Application Data

(63) Continuation-in-part of application No. 10/267,247, filed on Oct. 8, 2002, now Pat. No. 7,211,104.

(51) Int. Cl.
*A61F 7/02* (2006.01)
(52) U.S. Cl. ............... 607/104; 607/96; 607/114
(58) Field of Classification Search ........... 607/104–114
See application file for complete search history.

(56) References Cited

U.S. PATENT DOCUMENTS

| 267,435 A | 11/1882 | Leiter |
| 889,964 A | 6/1908 | Powell |
| 1,817,277 A | 8/1931 | Uhlig |
| 2,726,658 A | 12/1955 | Chessey |
| 3,648,765 A | 3/1972 | Starr |
| 3,683,902 A | 8/1972 | Artemenko et al. |
| 3,744,555 A | 7/1973 | Fletcher et al. |
| 3,869,871 A | 3/1975 | Rybalko et al. |
| 3,995,621 A | 12/1976 | Fletcher et al. |
| 4,149,541 A | 4/1979 | Copeland et al. |
| 4,184,537 A | 1/1980 | Sauder |
| 4,459,468 A | 7/1984 | Bailey |
| 4,587,959 A | 5/1986 | Ruderian |
| 4,691,762 A | 9/1987 | Elkins et al. |
| 4,703,957 A | 11/1987 | Blenkush |
| 4,844,072 A | 7/1989 | French et al. |
| 5,038,852 A | 8/1991 | Johnson et al. |
| 5,051,562 A | 9/1991 | Bailey et al. |
| 5,077,980 A | 1/1992 | Weber |
| 5,183,039 A | 2/1993 | Sarian et al. |

(Continued)

FOREIGN PATENT DOCUMENTS

DE    3410413 A1    10/1985

(Continued)

*Primary Examiner* — Roy Gibson
(74) *Attorney, Agent, or Firm* — Kang S. Lim

(57) ABSTRACT

The present invention relates to a replaceable module for use with a thermal contrast therapy systems. The replaceable module may be an automated thermal contrast therapy module which includes a casing, a manual mixing valve, an automated mixing valve, an automated mixing valve actuator, a temperature sensor, and an interface. A cold and a hot fluid are mixed to generate a therapy fluid. The therapy fluid may be output to a therapy bladder. The second replaceable module is a compression therapy module which includes a casing, an air pump, a pneumatic solenoid, and a pressure monitor. The casing may include a pressurized air pathway including an air outlet. The pump may pressurize the air within the pathway, and the solenoid may regulate the air pressure using feedback from the pressure sensor. Additionally, a pressure relief valve may release pressure if it gets above a safety threshold. The compression therapy module may also include a fluid pathway.

16 Claims, 33 Drawing Sheets

U.S. PATENT DOCUMENTS

| | | |
|---|---|---|
| 5,330,519 A | 7/1994 | Mason et al. |
| 5,344,436 A | 9/1994 | Fontenot et al. |
| 5,386,823 A | 2/1995 | Chen |
| 5,411,541 A | 5/1995 | Bell et al. |
| 5,441,533 A | 8/1995 | Johnson et al. |
| 5,476,489 A | 12/1995 | Koewler |
| 5,507,792 A | 4/1996 | Mason et al. |
| 5,562,604 A | 10/1996 | Yablon et al. |
| 5,647,051 A | 7/1997 | Neer |
| 5,711,155 A | 1/1998 | DeVilbiss et al. |
| 5,891,188 A | 4/1999 | Maytal |
| 5,894,615 A | 4/1999 | Alexander |
| 6,295,819 B1 | 10/2001 | Mathiprakasam et al. |
| 6,551,347 B1 * | 4/2003 | Elkins .......................... 607/104 |
| 2001/0039439 A1 | 11/2001 | Elkins et al. |

FOREIGN PATENT DOCUMENTS

| | | |
|---|---|---|
| GB | 2 175 496 A | 12/1986 |

* cited by examiner

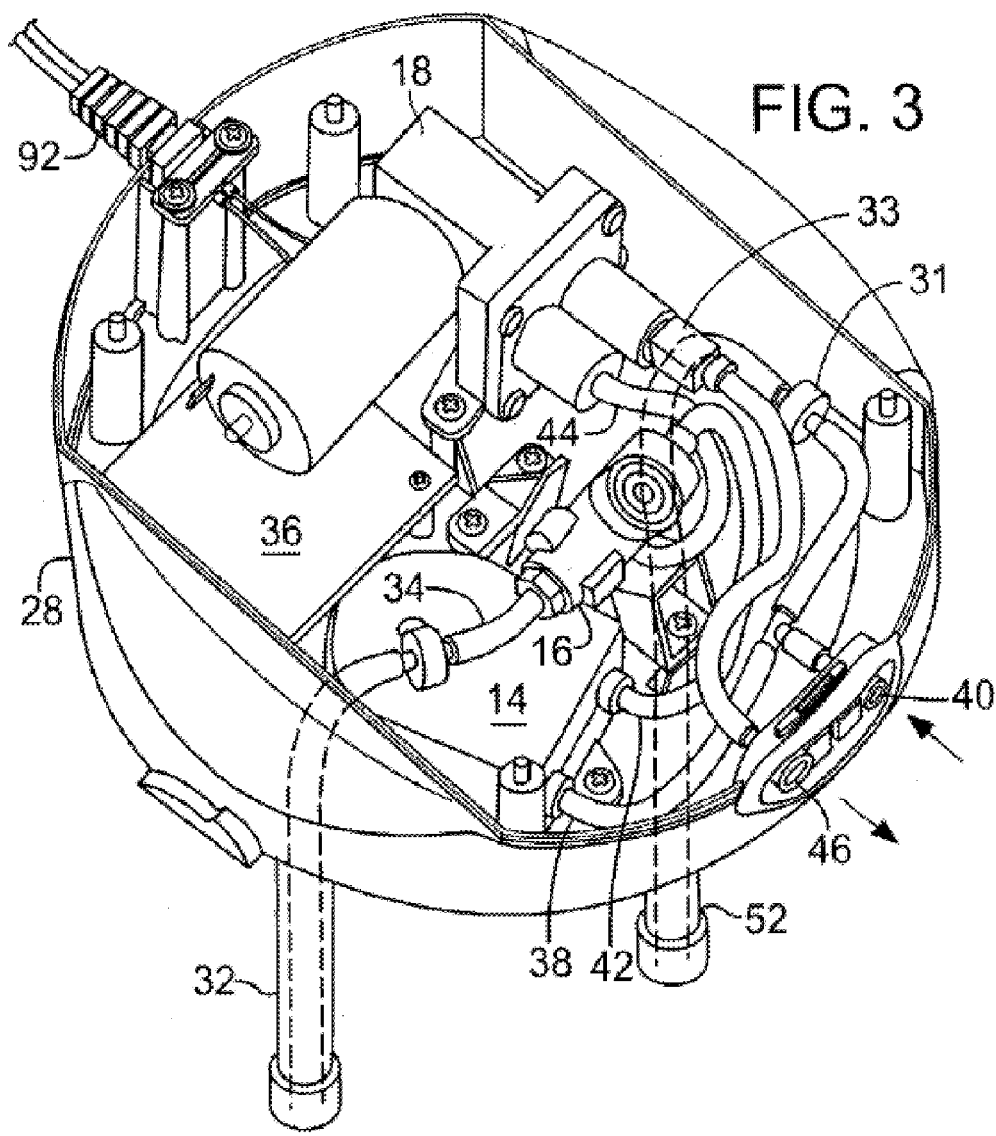

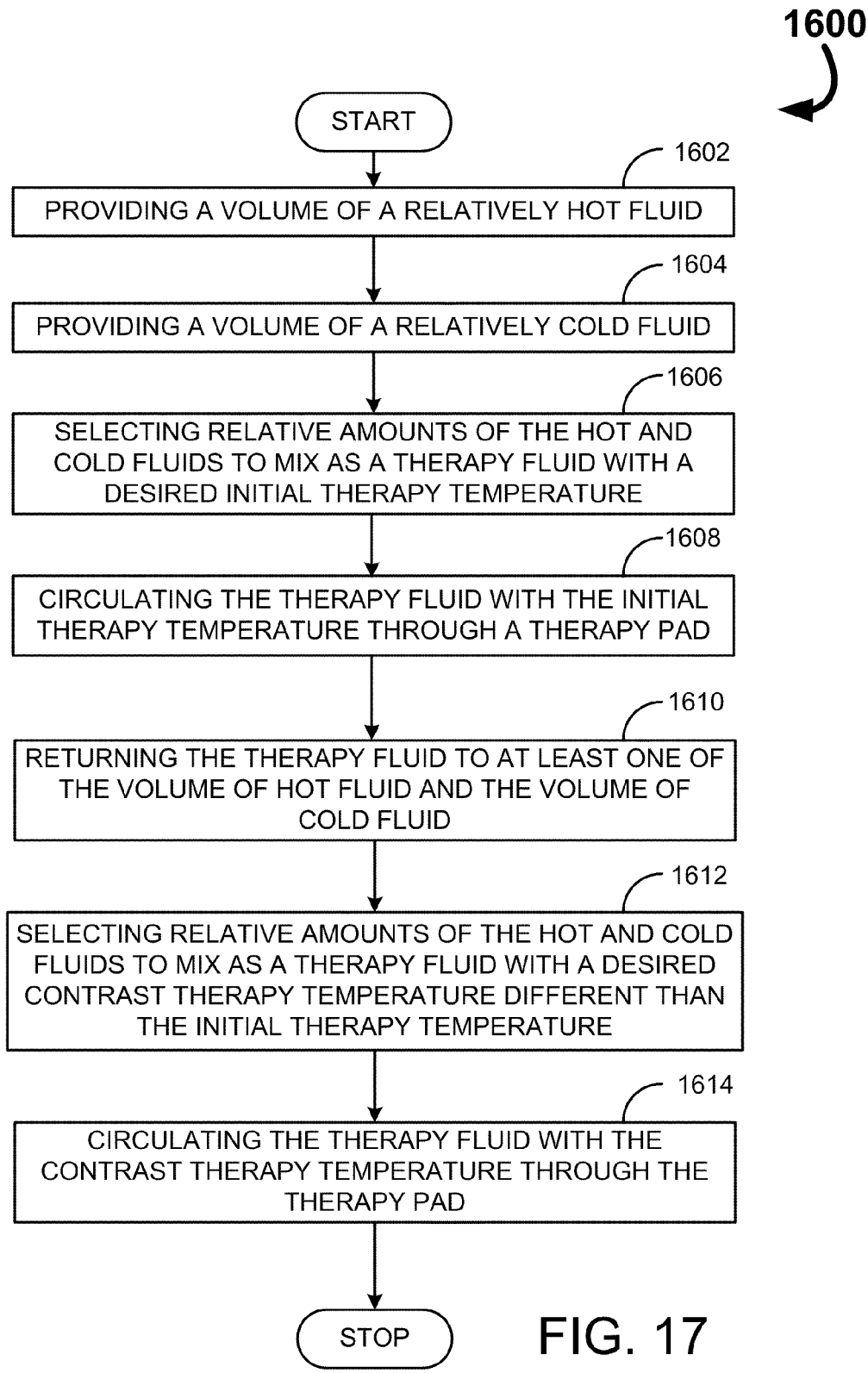

AUTOMATED TEMPERATURE CONTRAST AND DYNAMIC PRESSURE MODULES FOR A HOT OR COLD WRAP THERAPY SYSTEM

CROSS REFERENCE TO RELATED APPLICATIONS

This is a continuation-in-part of U.S. application Ser. No. 10/267,247 filed on Oct. 8, 2002, entitled "Contrast Therapy System and Method", now U.S. Pat. No. 7,211,104, which is hereby fully incorporated by reference.

BACKGROUND OF THE INVENTION

The present invention relates to a removable module for use in a contrast therapy system. The removable module enables a rapid transformation of a contrast therapy system to include a dynamic pressure system or automated contrast therapy. This transformative property enables reduced costs for a wide range of features to be included in a single lightweight contrast therapy system. The pressure module enables application of compression, massage and pulsation therapy to a therapy site. The automated contrast therapy module enables a programmable and automated temperature or contrast therapy.

Numerous thermal therapy devices that apply external treatments to the body are known in the art. Thermal or contrast therapy devices deliver or remove heat to a given therapy area for an effective amount of time in order to achieve a desired therapeutic result. Contrast therapy devices are used to reduce swelling or to encourage healing after swelling has receded. They are also used to soothe muscle and joint pain through the application of heat and compression therapy. Application of heat or cold may be used to heal and rehabilitate injuries to bone, muscle, ligaments, tendons and skin. Cold therapy may be used to reduce swelling, decrease pain, and promote healing of injured tissue. Heat therapy can be used to relax joint tissue, such as ligaments and tendons, to increase range of motion. Thermal therapy can also be used after surgery to reduce pain and swelling and promote healing.

The potential effectiveness of a hot or cold treatment increases as the level of control for the treatment increases. In particular, the effectiveness depends on the ability to control the temperature of the treatment. If cold treatments are too cold, they may cause skin and tissue damage. Similarly, if hot treatments are too hot, they may burn or otherwise damage the recipient. The effectiveness of a therapy also is dependent on the ease in which the therapy may be applied. If it is difficult for a therapy recipient to self apply a therapy, the opportunity to receive therapy may be diminished. Furthermore, if therapies are complicated and/or uncomfortable, a therapy recipient is less likely to undergo the therapy, although it may be beneficial.

Additionally, similar results may be obtained through compression therapy which may force excess fluids from the swollen body part. In conjunction with pressure pulsation, a massage-like effect may be obtained which may further reduce pain and/or healing time.

Typically, contrast therapy systems designed to provide pressure therapy, and manual and automatic contrast therapy are very cumbersome due to the required sizing and weight of the unit. Additionally, with the increase in features incorporated in current contrast therapy systems, there is an analogous increase in manufacturing and consumer costs. Both increased costs and bulk easily deter a potential user from engaging in contrast or pressure therapy.

Standard sized modules for distinct contrast therapy functionalities enable a single standard contrast therapy system to be built, thereby reducing costs. The modules may provide the desired functionality, and may be replaceable in order to enable any particular unit to provide the kind of therapy required, thereby minimizing unnecessary functions and reducing bulk of the unit. No such replaceable modules for contrast therapy units currently exist.

It is therefore apparent that an urgent need exists for a system for replaceable contrast therapy and pressure therapy modules for use in a contrast therapy system. These modules would be able to provide advanced functionality to contrast therapy systems without the associated increases in bulk and cost.

SUMMARY OF THE INVENTION

To achieve the foregoing and in accordance with the present invention, a replaceable module for use with a thermal contrast therapy systems and methods for module functionality are provided. Such systems are useful for providing effective pressure and contrast thermal therapy without the increased costs and bulk associated with such a system.

The present invention considers two exemplary replaceable modules. The first is an automated thermal contrast therapy module. The automated contrast therapy module includes a casing, a manual mixing valve, an automated mixing valve, an automated mixing valve actuator, a temperature sensor, and an interface.

A fluid pathway may exist within the casing. The casing includes at least one of a cold fluid inlet, a hot fluid inlet and a therapy fluid outlet. The manual mixing valve may mix a ratio of a cold fluid and a hot fluid to generate a manually mixed therapy fluid. Likewise, the automated mixing valve may mix a ratio of the cold and hot fluid, as well as the manually mixed therapy fluid to generate a final therapy fluid.

The automated mixing valve actuator includes a motor which rotates a screw gear, at least one gear coupled to the screw gear, and a position dial. As the screw gear rotates, the gears rotate in turn. The gear rotation may change the mixing ratio as well as rotate the position dial. The position dial includes grooves. At least one switch may sense the position of the position dial. The switch includes biasing arms, and the biasing arms flex in response to the grooves on the position dial.

The user may select a mode of mixing, such as manual mixing, automatic mixing and at least one contrast therapy program. The automated mixing valve actuator may control the automated mixing valve in response to the temperature of the final therapy fluid and the selected mode of mixing. A timing control may control timing of the at least one contrast therapy program. The automated contrast therapy module may output at least one of the manually mixed therapy fluid and the final therapy fluid to a therapy bladder.

The automated contrast therapy module includes a mounting bracket which fits a standard sized volume in the contrast therapy system. This enables the automated contrast therapy module to be removable from the contrast therapy system.

The second replaceable module is a compression therapy module, or pressure therapy module. The compression therapy module includes a casing, an air pump, a pneumatic solenoid, and a pressure monitor. The casing may include a pressurized air pathway including an air outlet. The pump may pressurize the air within the pathway, and the solenoid may regulate the air pressure using feedback from the pressure sensor. Additionally, a pressure relief valve may couple to the air pathway to release pressure if the air pressure gets above a safety threshold.

The casing may also include a fluid pathway with at least one of a cold fluid inlet, a hot fluid inlet and a therapy fluid outlet. A mixing valve may mix a ratio of the cold fluid and the hot fluid to generate the therapy fluid. Thus, the compression therapy module may output both the therapy fluid and the pressurized air to a therapy bladder.

The compression therapy module includes a mounting bracket, and wherein the mounting bracket fits a standard sized volume in the contrast therapy system. This enables the compression therapy module to be removable from the contrast therapy system.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which:

FIG. 3 is an isometric view of the fluid circuit of FIG. 2A housed within the lid portion of the contrast therapy system of FIG. 1;

FIG. 17 is an illustration of a method for administering contrast therapy to a therapy recipient in accordance with an embodiment of the present invention.

DETAILED DESCRIPTION OF THE INVENTION

Figure 1:
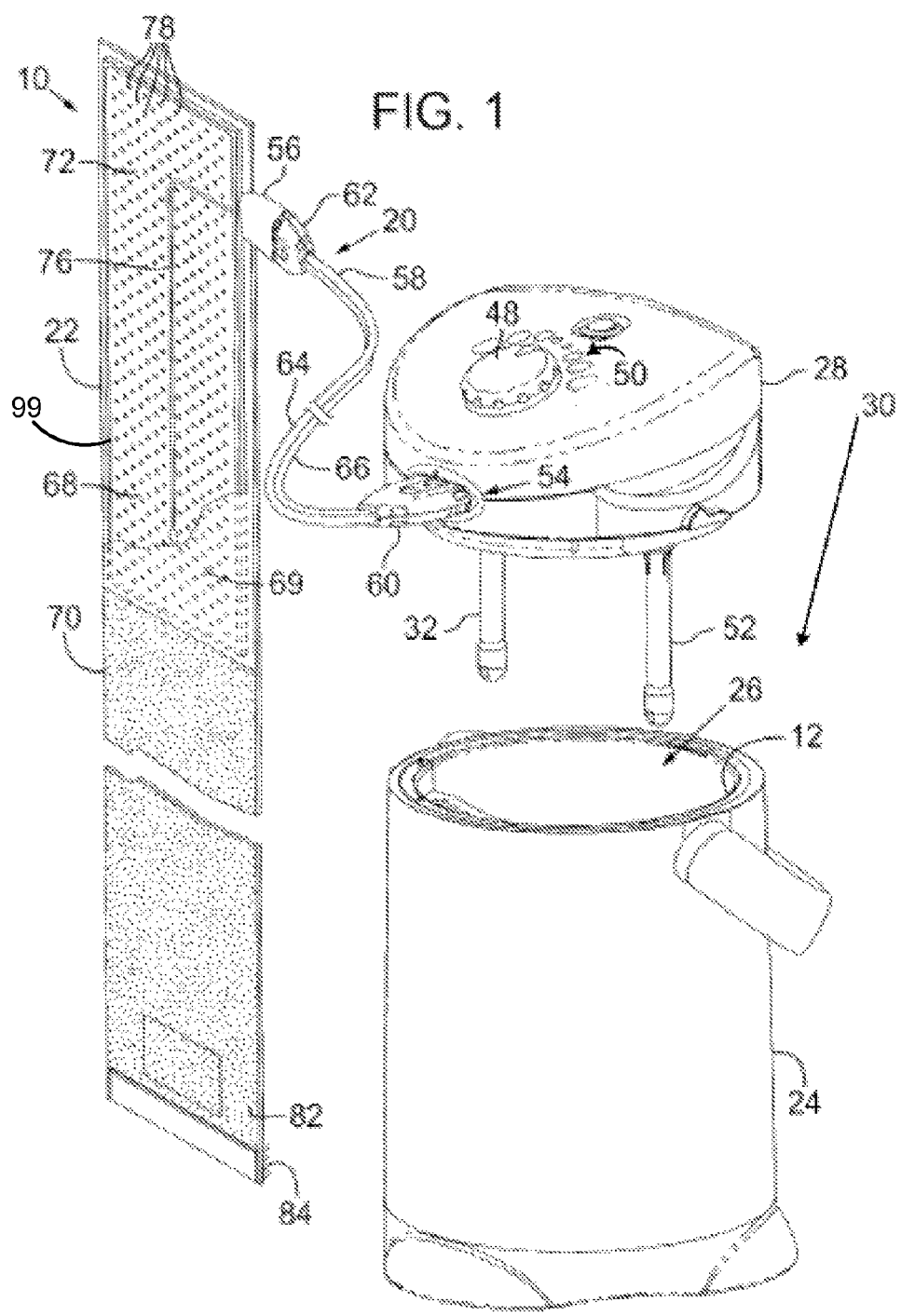
FIG. 1 is an isometric view of one embodiment of the contrast therapy system in accordance with the present invention.

The present invention will now be described in detail with reference to several embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention. The features and advantages of the present invention may be better understood with reference to the drawings and discussions that follow.

The present invention relates to removable modules for use in a contrast therapy system. The removable modules enable a rapid transformation of a contrast therapy system to include a pressure system or automated contrast therapy. This transformative property enables reduced costs for a wide range of features to be included in a single lightweight contrast therapy system. To facilitate discussion, FIGS. 1 through 8 show various views of the present contrast therapy system. FIGS. 9A to 12C provide illustrations of the automated contrast therapy module. This module enables a programmable and automated temperature or contrast therapy. FIGS. 13A through 15 show illustrations of the pressure, or compression therapy, module. This module enables application of compression, massage and pulsation therapy to a therapy site. FIG. 17 provides a logic table of a method for providing contrast therapy to a therapy recipient.

The contrast therapy system is described below in the context of providing "therapy" to a recipient, however, it should be understood that the Thermal Contrast Therapy Systems 10 are equally well suited for providing any combination of heat, cold, compression and support for what may be considered non-therapeutic purposes.

As described herein, the Contrast Therapy System 10 is capable of imparting a desired therapy temperature to a Therapy Pad 22 which may be applied to a therapy recipient. The system is capable of shifting the therapy temperature between hot and cold temperatures very quickly, which has proven to be beneficial. The precise temperature may be set at any temperature between controlled maximum and minimum temperatures. Furthermore, the contrast therapy system may be designed as a relatively small portable unit, as shown at 30 of FIG. 1, which is both easy and inexpensive to operate. The Portable Unit 30 includes a Container 24 and a Pump Unit 28. The Pump Unit 28 includes a Dial 48 and Indicia 50 to aid in the temperature control of the contrast therapy. The Container 24 may include a Cold Reservoir 12 and an Open End 26 that the Portable Unit 30 may fit into.

The following description of some embodiments of the present invention will be provided in relation to numerous subsections. The use of subsections, with headings, is intended to provide greater clarity and structure to the present invention. In no way are the subsections intended to limit or constrain the disclosure contained therein. Thus, disclosures in any one section are intended to apply to all other sections, as is applicable.

I. Fluid Circuit

Figure 2A:
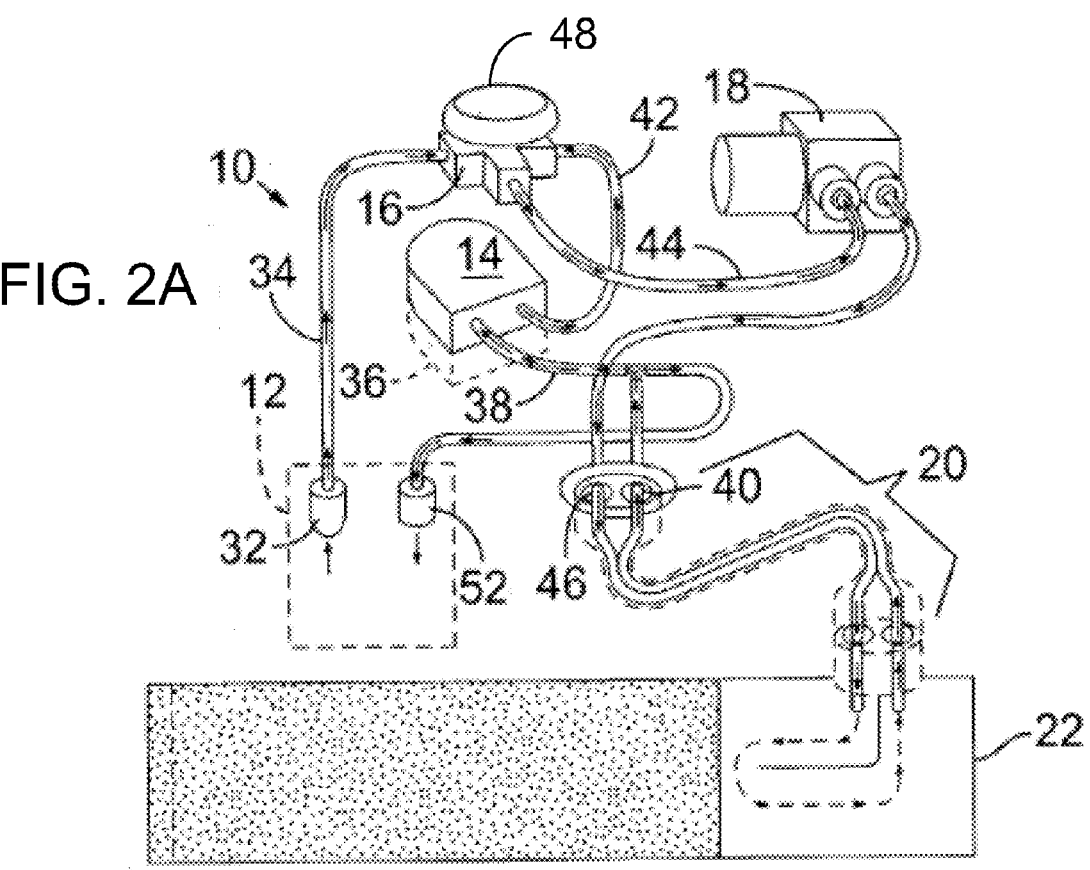
FIGS. 2A to 2B are schematic views of a fluid circuit for administering manual and automated temperature contrast therapy in accordance with an embodiment of the present invention.
Figure 2B:
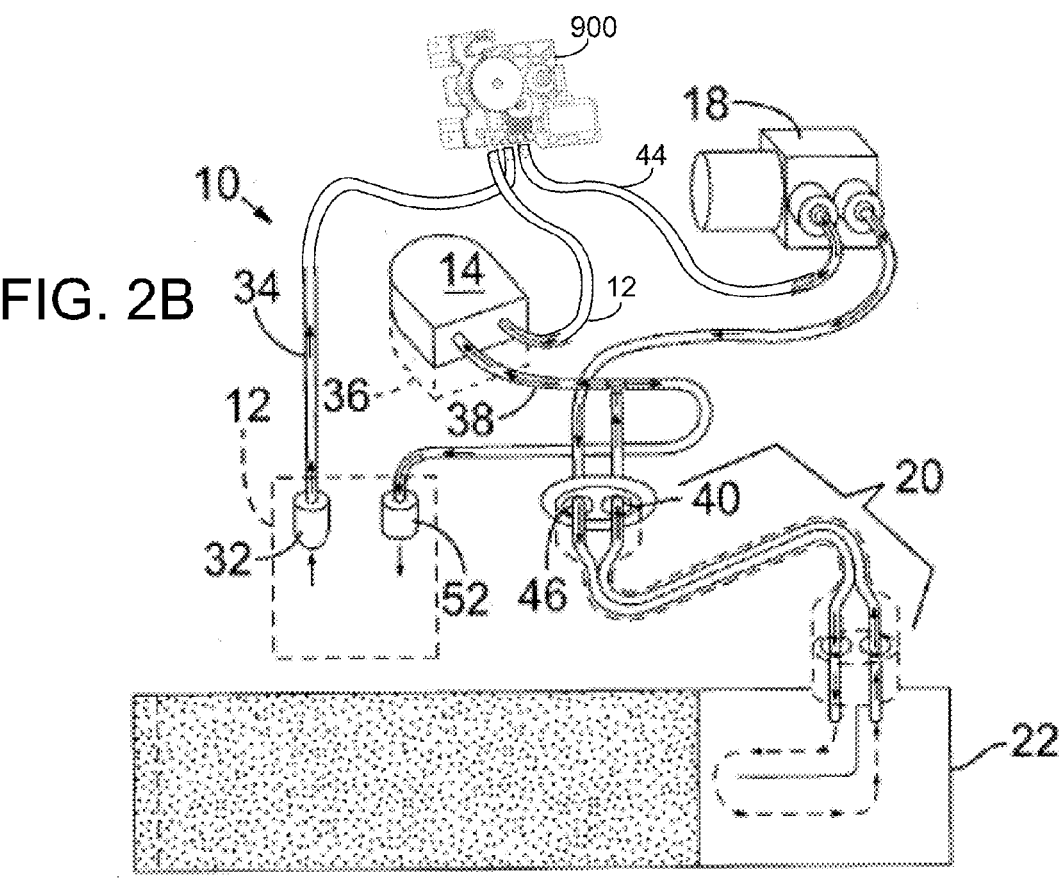
Figure 2C:
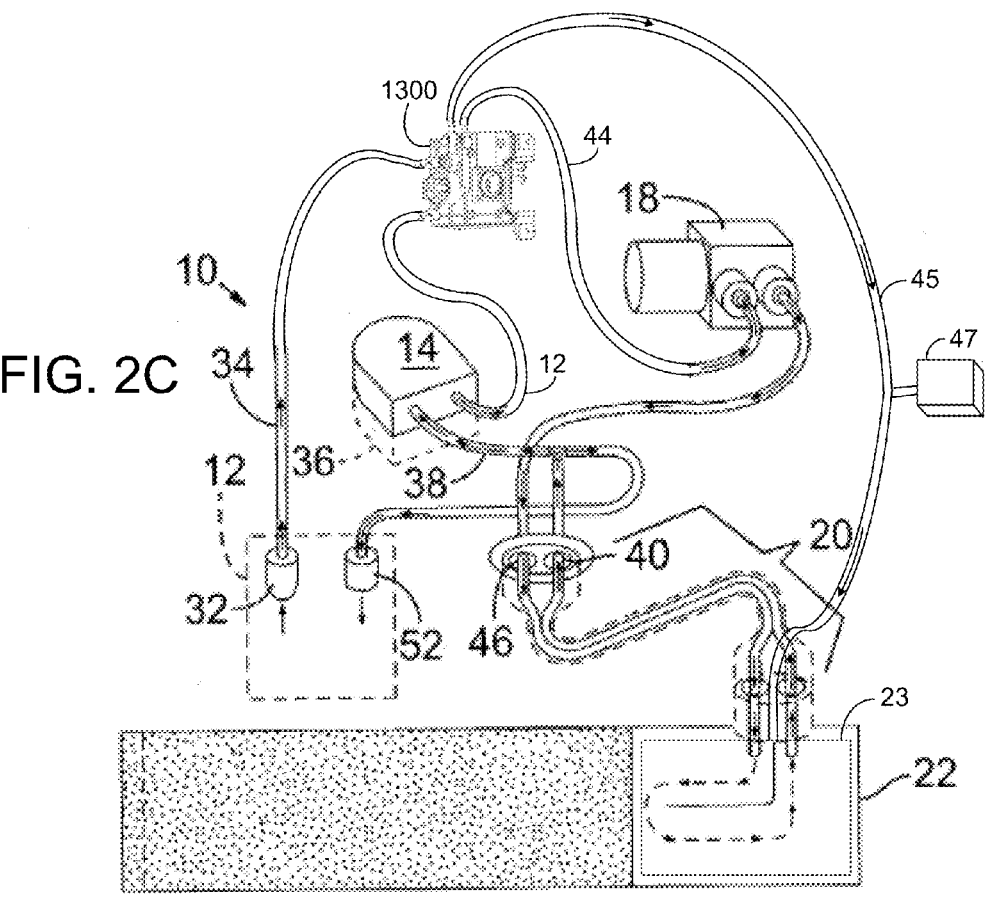
FIG. 2C is a schematic view of a fluid circuit for administering manual temperature contrast and automated compression therapies.

FIGS. 2A, 2B and 2C schematically show a fluid circuit of the Contrast Therapy System 10, and FIG. 3 shows such a circuit housed by the Pump Unit 28 of a Portable Control Unit 30. As illustrated in FIGS. 2A-2C and 3, the Contrast Therapy System 10 includes a Cold Reservoir 12, Hot Reservoir 14, Mixing Valve 16, Pump 18, Fluidic Coupling Assembly 20, and Therapy Pad 22. As described in detail below, the Contrast Therapy System 10 is designed to control the temperature of a therapy fluid that circulates through the Therapy Pad 22. In FIG. 2A, the Mixing Valve 16 selectively combines fluid received from the cold and hot reservoirs and passes the combined fluid to the Therapy Pad 22 as a therapy fluid. The Mixing Valve 16 may control the temperature of the therapy fluid, changing between hot and cold temperatures in a short period of time.

In FIG. 2B, the Automated Contrast Therapy Module 900 may replace the Mixing Valve 16. Likewise, in FIG. 2C the Compression Therapy Module 1300 may replace the Mixing Valve 16.

Cold Reservoir 12 is designed to hold a relatively cold fluid, which may be passed to the Mixing Valve 16 and eventually to the Therapy Pad 22. As shown in FIG. 1, Cold Reservoir 12 may include the Container 24 with an Open End 26 suitable for receiving the Pump Unit 28. The Container 24 and the Pump Unit 28 may be components of the Portable Control Unit 30. The Cold Reservoir 12 may be dimensioned to hold virtually any volume of fluid, and is shown as a 4.2 Liter receptacle. Of course, smaller Cold Reservoirs 12 may be used, for example, when increased portability is desired, and larger Cold Reservoirs 12 may be used when, for example, increased capacity is desired.

The temperature of the Cold Reservoir 12 may be controlled by various mechanisms. In some embodiments, the Cold Reservoir 12 is adapted to receive ice that may melt in the Cold Reservoir 12, and thus decrease the temperature of the fluid in the Cold Reservoir 12. As shown in FIG. 1, Container 24 has a large Open End 26 that is suitable for easily receiving ice. In some embodiments, the Cold Reservoir 12 may include a cooler for cooling the fluid held in the Cold Reservoir 12. Such a cooler may include a compressor and a refrigerant or similar cooling mechanism. It is within the scope of the invention, however, to use virtually any other suitable method for cooling the fluid held in Cold Reservoir 12. The Cold Reservoir 12 may include insulation to limit heat transfer between the fluid held by the Cold Reservoir 12 and the external environment.

The minimum temperature of the fluid in Cold Reservoir 12 is usually limited to approximately 32 to 45 degrees Fahrenheit, although such a limitation is not necessary. In particular, it has been found that a temperature of about 32 to 45 degrees Fahrenheit is an appropriate minimum temperature. Although water is usually used as the fluid, it is within the scope of the invention to use other suitable fluids. Such fluids may be selected for particular applications based on their specific heat, viscosity, freezing point, etc.

The Contrast Therapy System 10 may include an Intake 32 for drawing fluid from the Cold Reservoir 12. The drawn fluid may pass through a Fluid Path 34 between Cold Reservoir 12 and Mixing Valve 16, as is schematically shown in FIG. 2A. Fluid Path 34, as well as other Fluid Paths described herein, may utilize ⅛ I.D. inch flexible tubing, or may alternatively implement another suitable fluid transport mechanism. For example, some or all of the Fluid Paths 34 may alternatively be defined by inflexible fluid conduits. The Fluid Path 34, or other fluid channels such as Intake 32, may include filters, flow restrictors, and/or check valves. Filters may help prevent flow blockages resulting from jammed ice or other substances, and check valves may be used to prevent backflow in the system. The rate of fluid flow may be at least partially controlled by flow restrictors.

Hot Reservoir 14 is designed to hold a relatively hot fluid, which may be passed to the Mixing Valve 16, Automated Contrast Therapy Module 900, or Compression Therapy Module 1300 and eventually to the Therapy Pad 22. Fluid in the Hot Reservoir 14 may be heated by a Heater 36, which may be positioned adjacent the Hot Reservoir 14, or may be incorporated into the Hot Reservoir 14. The Hot Reservoir 14 may be dimensioned to hold virtually any volume of fluid, and is shown dimensioned to hold a volume of approximately 20 to 30 cubic centimeters. It should be understood that the Hot Reservoir 14 may be smaller or larger, depending on the desired use and the other components of the contrast therapy system. Additionally, the Hot Reservoir 14 may be insulated to prevent heat loss from the Hot Reservoir 14 fluid to the external environment.

Heater 36 may be configured so as to achieve a suitable balance of power consumption and heat generation. It has been found that a heater of approximately 280 Watts is appropriate for heating a volume of approximately 20 to 30 cubic centimeters under normal conditions. It should be understood that more powerful and less powerful Heaters 36 may be used. Similarly, more than one heater or type of heater may be used.

The flow rate of fluid through the Hot Reservoir 14 may correspond to the temperature of treatment being applied, with greater flow rates occurring during hotter treatments. During some hot treatments, Heater 36 may have limited time to increase the temperature of the fluid because the fluid quickly passes through the Hot Reservoir 14, and thus, the heater should be powered so as to increase the temperature a desired amount within that constrained timeframe. However, the Heater 36 does not need to completely heat the fluid from a minimum temperature to a maximum temperature in such a timeframe, although it is within the scope of the invention to do so. The Hot Reservoir 14 receives fluid from the Therapy Pad 22, and when a hot treatment is being applied, the return fluid may already be partially heated, decreasing the magnitude of heating required from Heater 36. Thus, the net temperature of the fluid may incrementally increase as it repeatedly circulates through the Hot Reservoir 14. Nevertheless, a more powerful heater may increase the rate fluid increases temperature in the Hot Reservoir 14 and/or the maximum temperature of the fluid, thus decreasing the time required to change from a cold treatment to a hot treatment. The maximum temperature of the fluid in Hot Reservoir 14 is usually limited to approximately 100 to 110 degrees Fahrenheit, although such a limitation is not required. In particular, it has been found that a temperature of about 105 degrees Fahrenheit is appropriate.

As illustrated in FIGS. 2A-2C and 3, Hot Reservoir 14 receives fluid via a Fluid Path 38 coming from a Bulkhead Input 40. As described below, Bulkhead Input 40 receives fluid returning from the Therapy Pad 22. The returning fluid may be directed so that fluid may go to at least one of the Hot Reservoir 14, via Fluid Path 38, and the Cold Reservoir 12, via a Return 42. In some embodiments, the Hot Reservoir 14 may be housed within Pump Unit 28, which may be securely fit to Open End 26 of Container 24. Heater 36 may be controlled by an internal control system, external control system, or no control system whatsoever. If present, a control system may regulate the maximum temperature of fluid in the Hot Reservoir 14, for example. Such a control system may also be designed to maximize heating efficiency to limit energy requirements.

Contrast Therapy System 10 may include a Power Supply, such as 92 of FIG. 3, for providing power to various components of the system, such as a heater, cooler, pump, thermostat, display, etc. In some embodiments, the power supply may provide alternating current, while in other embodiments, the power supply may provide direct current. Some embodiments may be configured to operate with either AC or DC power. For example, the contrast therapy system may include a DC heater and pump designed to draw power from either a battery or an electrical outlet via an AC/DC converter. Batteries used to power the contrast therapy system may be externally connected to the system, and/or housed within the system. The contrast therapy system may be powered from alternative power sources as well.

II. Mixing Valve

The Contrast Therapy System 10 includes the Mixing Valve 16 for receiving a selected ratio of the hot and cold fluids from the Hot Reservoir 14 and Cold Reservoir 12. The Mixing Valve 16 is operable to deliver a therapy fluid with a therapy temperature that is determined by the selected ratio. In other words, Mixing Valve 16 may adjustably control the amount of hot fluid from the Hot Reservoir 14 and the amount of cold fluid from the Cold Reservoir 12 that mix together. The ratio may be 100% hot fluid from the Hot Reservoir 14, in which case the resulting therapy fluid would have a therapy temperature substantially equal to the temperature of fluid leaving the Hot Reservoir 14 (maximum temperature). The ratio may alternatively be 100% cold fluid from the Cold Reservoir 12, in which case the resulting therapy fluid would have a therapy temperature substantially equal to the temperature of fluid leaving the Cold Reservoir 12 (minimum temperature). Any temperature in between the maximum and minimum temperature may be achieved by adjusting the ratio via Mixing Valve 16.

The mixing valve is linked to the Cold Reservoir 12 and the Hot Reservoir 14 by respective Fluid Paths 34 and 42. In some embodiments, one or both of Fluid Paths 34 and 42 may include a pump, although no pump is required. The Mixing Valve 16 outputs therapy fluid to a Fluid Path 44 that leads to the Bulkhead Output 46, and eventually to the Therapy Pad 22. A Pump 18 may be included between the Mixing Valve 16 and the Therapy Pad 22, as shown in FIGS. 2A-2C and 3 and described below. As with the other Fluid Paths of the contrast therapy system, these Fluid Paths may include flow restrictors, check valves, filters, over-pressure switches, and/or other components. For example, Check Valve 31 and Over Pressure Switch 33 are illustrated in FIG. 3. The flow paths may include flexible rubber tubing that is approximately ⅛ inch inner diameter.

As shown in FIGS. 1 and 2A, the Mixing Valve 16 may be controlled by a Dial 48 that adjusts the ratio of hot and cold fluids delivered from the mixing valve. The Dial 48 may be associated with Indicia 50 that indicate a relative magnitude of a desired therapy temperature. For example, Indicia 50 may include a series of icons representing relative temperatures. A large red dot may represent the hottest therapy temperature, with red dots decreasing in size representing decreasing temperatures. Similarly, a large blue dot may represent the coldest therapy temperature, with blue dots decreasing in size representing increasing temperatures. The Dial 48 positioned to point to the large red dot may correspond to a mixing valve position that yields a ratio of 100% hot fluid. As the Dial 48 is turned through the progressively smaller red dots, and then through the progressively larger blue dots, the ratio may yield a therapy fluid with a continually increasing percentage of cold fluid.

In some embodiments, the Contrast Therapy System 10 may include a thermostat that automatically selects the ratio of hot and cold fluids delivered from the Mixing Valve 16. For example, the thermostat may be designed to receive manual input of a desired therapy temperature, and adjust the mixing valve to yield a therapy fluid with that temperature. Accordingly, the thermostat may include a temperature measuring device (not shown), such as a thermostat, thermometer, thermocouple, etc. The temperature measuring device may monitor the temperature of the therapy fluid as the thermostat adjusts the mixing valve to yield the desired therapy temperature. The temperature measuring device may cooperate with a temperature display to present the temperature of the therapy fluid. The thermostat may be programmable to automatically change the therapy temperature at a desired time or event by adjusting the ratio of hot and cold fluids delivered from the mixing valve. For example, the thermostat may be programmed to provide alternating hot therapies that last for five minutes at 105 degrees Fahrenheit and cold therapies that last for 5 minutes at 40 degrees Fahrenheit. It should be understood that the thermostat may be programmed for therapies of different durations and/or temperatures.

As shown in FIGS. 2A-2C and 3, the Contrast Therapy System 10 may include a Pump 18 for circulating fluid through the system. As illustrated, the Pump 18 interposes the Mixing Valve 16 and the Bulkhead Output 46, although the Pump 18 may be positioned elsewhere. Similarly, more than one pump may be utilized. As is shown, the Pump 18 may be integrated into the Pump Unit 24 of the Portable Control Unit 30. The Pump 18 may be powered according to the desired application, and a 4 Watt pump capable of pumping 300 cubic centimeters of fluid per minute has been found to be suitable. The Pump 18 may be a reciprocating pump, a rotary pump, or virtually any other suitable pump.

In some embodiments, the Pump 18 may be configured to pulse the therapy fluid through the Therapy Pad 22. Such a pulsing action may be translated into a therapeutic massage via the Therapy Pad 22. As the pulsing fluid circulates through the Therapy Pad 22, the Therapy Pad 22 may vibrate. Pumps designed to pulse fluid may be further enabled to adjust the relative magnitude of the pulsing to correspond to different intensities of therapeutic massages. The relative intensity may be automatically, or manually, coordinated to correspond to a particular temperature of treatment. For example, a vigorous massage may be applied during a hot treatment while a milder massage is applied during a subsequent cold treatment.

Also of note is the Air Tube 45 which provides compression air to a Compression Air Bladder 23 within the Therapy Pad 22. In some embodiments, a High Pressure Switch 47 may be coupled to the Air Tube 45. The High Pressure Switch 47 may be electrical and/or mechanical, and may sense over pressurization of the Compression Air Bladder 23. If over pressure is detected, a signal may be sent to the system to shut it down.

III. Fluidic Coupling Assembly

Figure 4:
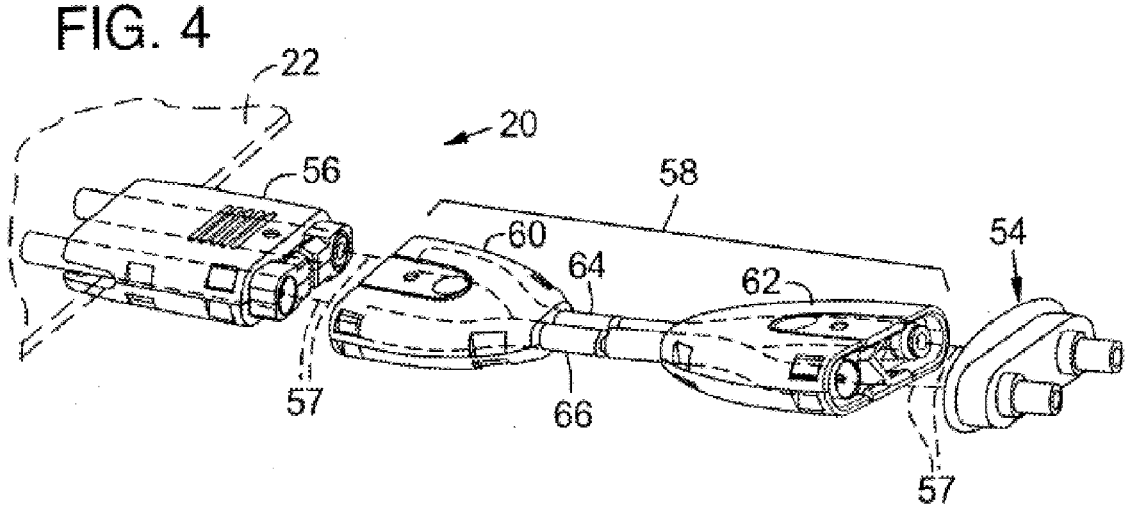
FIG. 4 is an isometric view of a fluidic coupling assembly in accordance with an embodiment of the present invention.

The Contrast Therapy System 10 may include the Fluidic Coupling Assembly 20 to selectively couple and decouple the Portable Control Unit 30 and the Therapy Pad 22. As shown in FIG. 4, the Fluidic Coupling Assembly 20 usually includes a Bulkhead 54, which is in fluid communication with the Mixing Valve 16, a wrap Connector 56, and a Reversible Tubing Assembly 58 for linking the Bulkhead 54 to the Connector 56. The Reversible Tubing Assembly 58 includes a First Tube-Set Connector 60 and a Second Tube-Set Connector 62 that are functionally equivalent to one another. Of course the First Tube-Set Connector 60 and the Second Tube-Set Connector 62 may be designed to differ from one another to limit connectivity as desired. First Tube-Set Connector 60 and Second Tube-Set Connector 62 are linked by Fluid Paths 64 and 66.

Bulkhead 54, First Tube-Set Connector 60, Second Tube-Set Connector 62, and Connector 56 each include one male valve and one female valve, which are configured to mate with a corresponding female and male valve, for example, as shown by dotted lines 40 in FIG. 4. The Bulkhead 54 and the Connector 56 are each configured to releasably receive either the First Tube-Set Connector 60 or the Second Tube-Set Connector 62. Therefore, Tubing Assembly 58 is completely reversible. For example, the Bulkhead 54 and the First Tube-Set Connector 60 may be coupled so that the Bulkhead's 54 male valve mates with the First Tube-Set Connector's 60 female valve, and the Bulkhead's 54 female valve mates with the First Tube-Set Connector's 60 male valve. Likewise, the Connector 56 and the Second Tube-Set Connector 62 may be coupled so that the bladder Connector's 56 male valve mates with the Second Tube-Set Connector's 62 female valve, and the bladder Connector's 56 female valve mates with the Second Tube-Set Connector's 62 male valve. Because the tubing assembly is reversible, the above described connection may be reversed. For example, if the First Tube-Set Connector 60 is connected to the Bulkhead 54, the Second Tube-Set Connector 62 is available for connection to the Connector 56, but if the Second Tube-Set Connector 62 is connected to the Bulkhead 54, the First Tube-Set Connector 60 is available for connection to the bladder Connector 56. In either case, such arrangements permit fluid to flow from the Portable Control Unit 30 to the Therapy Bladder 99, and then return back to the Portable Control Unit 30.

The male and female valves of each of the above described components are equally spaced from one another. Therefore, male and female valves from one component may align with female and male valves from a corresponding component. Furthermore, Bulkhead 54 is complementarily configured relative to both the First and Second Tube-Set Connectors 60, 62 to facilitate securing either the First Tube-Set Connector 60 or the Second Tube-Set Connector 62 to the Bulkhead 54. Similarly, either the First Tube-Set Connector 60 or the Second Tube-Set Connector 62 may be secured to the bladder Connector 56. The male and female valves are designed to prevent fluid flow unless they are mated with one another, thus limiting leakage when disconnecting the Reversible Tubing Assembly 58 from the Portable Control Unit 30.

The configuration of the Fluidic Coupling Assembly 20 facilitates easy connection and disconnection of a plurality of Portable Control Units 30, Tubing Assemblies 58, and thermal Therapy Pads 22. For example, the same Portable Control Unit 30 may be used with a variety of different Therapy Pads 22, which may be individually configured to treat different areas of a recipient's body. The Fluidic Coupling Assembly 20 facilitates quick and easy coupling and decoupling, and the leak reducing male and female valves help limit spillage during such coupling and decoupling.

IV. Therapy Pad

Figure 5:
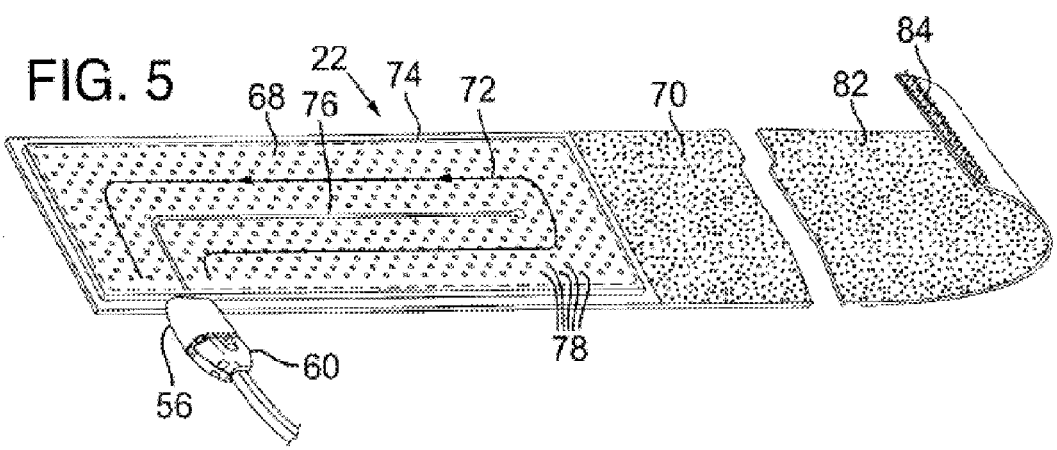
FIG. 5 is an isometric view of a contrast therapy pad in accordance with an embodiment of the present invention.

FIG. 5 shows Therapy Pad 22 apart from the remainder of the contrast therapy system. As described above, the Therapy Pad 22 may be easily coupled and decoupled from the Reversible Tubing Assembly 58, which allows various different Therapy Pads 22 to be used with the same control unit. Each Therapy Pad 22 is designed to receive therapy fluid from the mixing valve, such as through the fluidic coupling assembly, and return the therapy fluid to at least one of the hot reservoir and the cold reservoir (as shown schematically in FIGS. 2A-2C). The Therapy Pad 22 returns fluid to the control unit, and the returned fluid may be recirculated. Depending on the type of therapy being applied, returned fluid may be heated and/or cooled at the control unit. The contrast therapy system may include a return valve that selectively directs return fluid to the hot reservoir and/or the cold reservoir, or the return fluid may be allowed to naturally flow to the lower pressure region.

Figure 6:
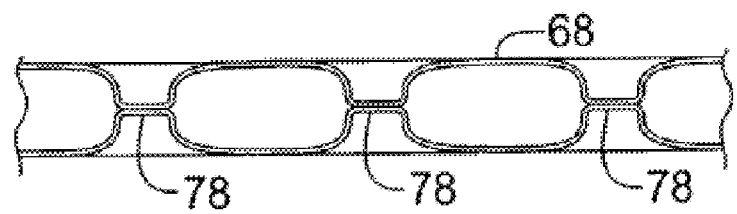
FIG. 6 is a cross-sectional view of a portion of the contrast therapy pad of FIG. 5.

In some embodiments, the Therapy Pad 22 includes an active Thermal Exchange Bladder 68 and an Elastic Wrap 70 that is connected to the Thermal Exchange Bladder 68. The Thermal Exchange Bladder 68 may include a flexible membrane of opposing faces that are welded together to define a channel system for directing the flow of therapy fluid along a desired Fluid Path 72 within the Thermal Exchange Bladder 68. For example, the faces are usually welded along a common Outer Perimeter 76, sealing the faces together. A division weld 76 may direct fluid through a substantial portion of the pad before returning to the control unit. The Thermal Exchange Bladder 68 may also include a plurality of Intermittent Welds 78, which limit inflation of the bladder, as shown in FIG. 6, which is a cross-sectional view of a portion of the exchange bladder.

The Thermal Exchange Bladder 68 facilitates thermal exchange between a therapy site and the therapy fluid. For example, when a cold therapy is administered, heat from a recipient's body may heat the therapy fluid, which in turn cools the therapy site. Similarly, when a hot therapy is administered, the therapy fluid may transfer heat to the therapy site. The therapy may be enhanced by moistening the bladder to provide a moist therapy. Furthermore, the fluid may also be pulsed through the bladder, adding a therapeutic massage aspect to the treatment.

In the illustrated embodiment, Therapy Pad 22 is dimensioned to hold approximately 26 cubic centimeters of fluid. However, the volume of the Therapy Pad 22 may be controlled by changing the size of the Therapy Pad 22, and/or the amount of inflation the intermittent welds allow. Furthermore, the Therapy Pad 22 may be constructed from an at least partially elastic material, such as urethane, which may permit the volume to change in response to the pressure of fluid within the bladder. In some embodiments, the bladder may include a less elastic material that helps prevent stretching, such as a vinyl/urethane blend.

Figure 6A:
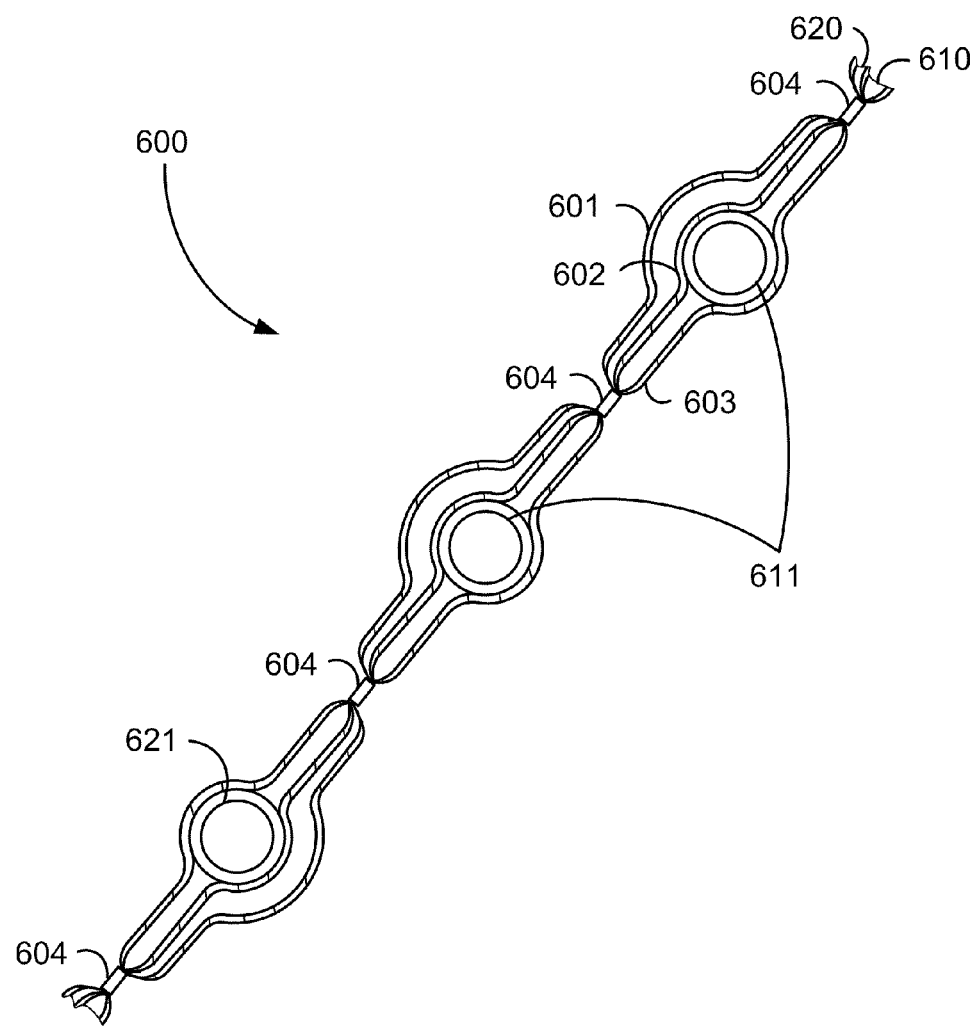
FIG. 6A is a cross-sectional view of a portion of a compression and contrast therapy pad of FIG. 5.

FIG. 6A shows a cross sectional view of a fluid Bladder 600 with a compression layer for use with the compression module. In some embodiment, the Bladder 600 may include a First Membrane 601, a Second Membrane 602 and a Third Membrane 603 sealed around the Outer Perimeter 605. The First Membrane 601 and Second Membrane 602 may define the Pneumatic Layer 620 volume for pressurized expansion (compression layer). The Second Membrane 602 and Third Membrane 603 may define the Fluid Layer 610 volume for therapeutic fluid flow. The First Membrane 601, Second Membrane 602 and Third Membrane 603 may additionally be welded together at the Intermittent Welds 604 to provide durability to the compression Bladder 600 and prevent over inflation of the Fluid Layer 610 or the Pneumatic Layer 620. The First Membrane 601, Second Membrane 602 and Third Membrane 603 may be made of the same material, or may include different materials depending upon the characteristics desired. For instance, it may be desired that the First Membrane 601 be more elastic than the Second Membrane 602 or Third Membrane 603, thereby allowing for greater expansion of the Pneumatic Layer 620.

The Fluid Layer Connector Tubes 611 may be seen inserting the Amalgamated Bladder 600 between the Second Membrane 602 and Third Membrane 603, thereby providing therapy fluid to the Fluid Layer 610. Likewise, the Pneumatic Connector 621 may insert between the Second Membrane 602 and First Membrane 601, thereby providing pressure control to the Pneumatic Layer 620.

Additionally, the compression Bladder 600 may vary in shape and size in order to accommodate particular therapeutic desires.

In some embodiments, the Amalgamated Bladder 600 may be constructed with disposable materials. For example, Bladder 600 configured for a single use may be constructed from disposable materials, which are usually less expensive than reusable materials. The disposable Bladder 600 may be particularly useful in emergency, trauma, or post surgery situations, in which a therapy recipient may bleed onto the Bladder 600. The ability to control the temperature of the Fluid Layer 610, either reusable or disposable, may increase the Bladder's 600 effectiveness as a wound dressing. Disposable materials may include less resilient versions of reusable materials and/or completely different materials. In some embodiments, disposable materials may include apertured, breathable, elastomeric and/or embossed films, as well as nonwoven laminates. Bladder 600 may alternatively be configured to be washable, such as by a laundry machine, and therefore may be sanitarily reused.

As shown in FIG. 5, fluid may enter the bladder at bladder Connector 56, flow around the division weld and the Intermittent Welds 78, and leave the bladder at the bladder Connector 56. It is within the scope of the invention to reconfigure the bladder to accommodate different flow paths. For example, the division weld, or plural division welds, may be used to direct the fluid through a series of switchbacks before returning to the output of the bladder Connector 56. Small breaks may be included in the division weld to permit alternative flow paths if a primary flow path is blocked.

Figure 7:
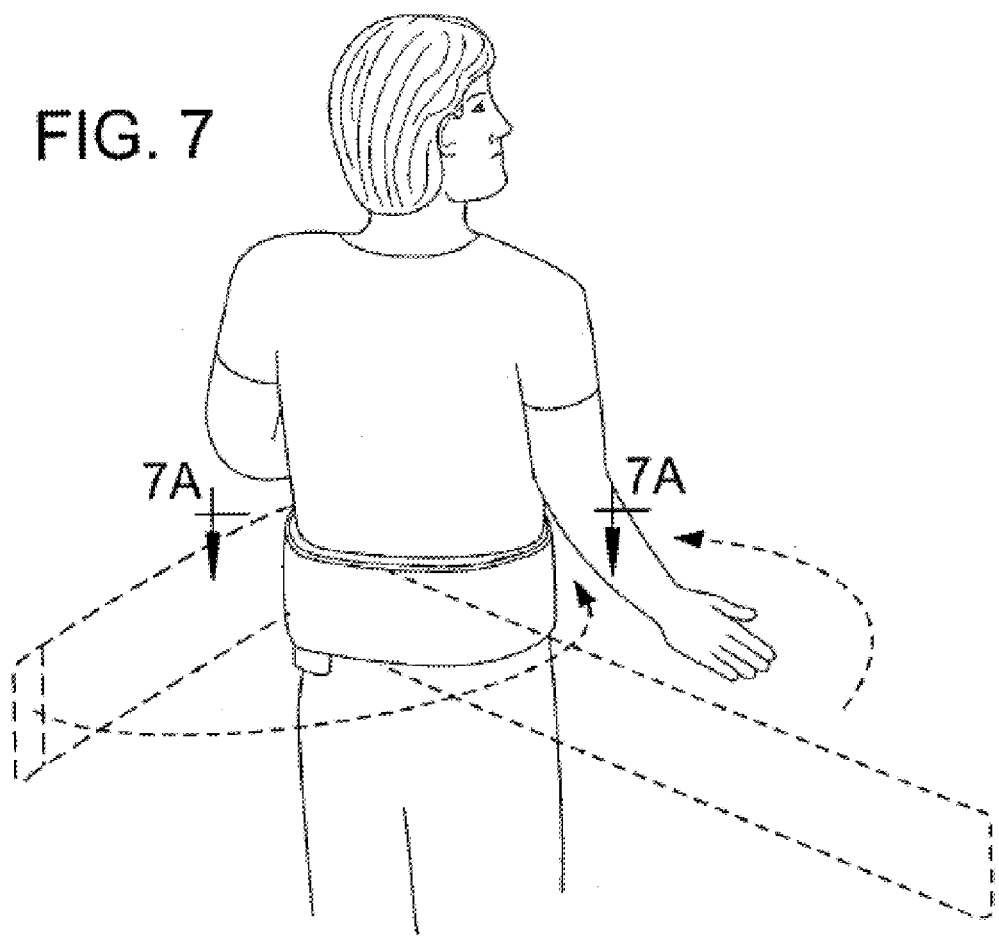
FIG. 7 is an isometric view of a therapy pad wrapped around a therapy recipient.

Elastic Wrap 70 is shown connected to the Thermal Exchange Bladder 68. The Elastic Wrap 70 may be configured to adjustably wrap around the Thermal Exchange Bladder 68 and compress the Thermal Exchange Bladder 68 around a therapy site. Compression helps induce contact of the bladder with the therapy site, which may promote efficient and even thermal transfer. Furthermore, the wrap is a compressive element in and of itself. When used in conjunction with the bladder, it keeps the bladder in contact with the therapy site, and it may also help reduce swelling through its own inherent compressibility. The wrap is continuously adjustable, meaning it may be repeatedly tightened and loosened to various levels of compression, as shown in FIG. 7. The wrap may be used in tandem with the bladder to wrap a therapy site in a variety of ways, thus providing extreme flexibility in the types of treatments that may be administered to a wide range of different therapy sites.

Figure 7A:
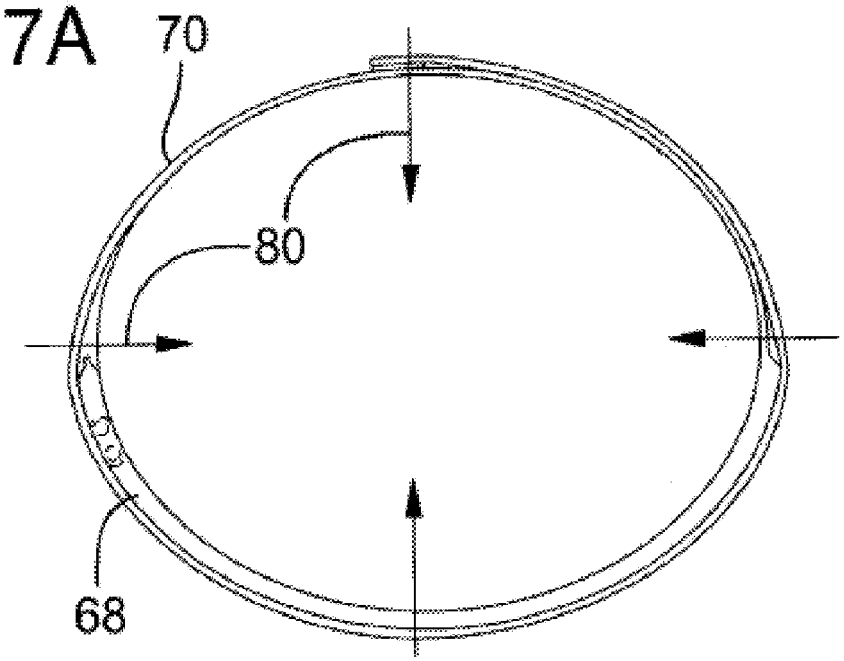
FIG. 7A is a cross-sectional view of the therapy pad of FIG. 7 wrapped around the therapy recipient.

Wrap 70 is elastic; it may be stretched and naturally return to an unstretched disposition. When stretched, the wrap is at an increased tension, which may be used to compress a Therapy Pad 22 around a therapy site, as shown in FIG. 7A. Force vectors 80 schematically represent the compressive force resulting from the wrap. The magnitude of the compressive force may be selected by adjusting the amount the wrap is stretched. As the wrap is increasingly stretched around a therapy site, the compressive force the wrap applies increases. Similarly, the wrap may be loosened, decreasing the magnitude of the compressive force. The amount of elasticity a particular wrap has may be selected according to a desired application, or range of applications. In some embodiments, the wraps are designed to stretch to approximately 150%-200% of their unstretched length, however less elastic and more Elastic Wraps 70 may be used. The wraps may be variously sized, and are usually at least as long as their corresponding bladder when unstretched. As illustrated in FIG. 5, the unstretched wrap is six times as long (54 inches) as the bladder (18 inches). Because of the elastic configuration of the wrap, wrapping techniques known to physical therapists, physical trainers, and sports physicians may be used in conjunction with the Therapy Pad 22 to achieve a wide variety of therapeutic benefits.

As shown in FIG. 5, Elastic Wrap 70 is permanently connected to Thermal Exchange Bladder 68. The wrap may be connected by stitching, an adhesive, and/or another suitable fastener. In some embodiments, the bladder is connected to the wrap via an optional mesh envelope, shown in dashed lines at 69. In such embodiments, the envelope may be permanently connected to the wrap, and the bladder may be selectively positioned within the mesh envelope. The mesh envelope may include a fastening face configured to selectively fasten with a complimentary fastener of the wrap. The wrap may alternatively be removably connected to the bladder, such as by hook and loop connectors. By permanently connecting the wrap to the bladder, such as by stitching or configuring an envelope to securely hold the bladder relative to the wrap, the wrap and the bladder may cooperate to provide a compressive force, as described herein. Furthermore, the combination has proven to be much easier to apply than separated Therapy Pads and wraps, and thus is more versatile.

The wrap usually includes a surface of loops 82 that are adapted to detachably receive complementary hooks 84. The hooks and loops are positioned, so that the hooks may engage the loops when the wrap is wrapped around a therapy site, as shown in FIGS. 7 and 7A. The wrap may be adjusted to a desired tension and a corresponding level of compressive force that may be fixed by engaging the hooks and the loops together. The hooks and loops may subsequently be disengaged, so that the tension may be adjusted, for instance, and reengaged at will. In some embodiments, a wrap lock may alternatively be used to secure the wrap.

In some embodiments, the Therapy Pads 22 may be constructed with disposable materials. For example, pads configured for a single use may be constructed from disposable materials, which are usually less expensive than reusable materials. Disposable Therapy Pads 22 may be particularly useful in emergency, trauma, or post surgery situations, in which a therapy recipient may bleed onto the Therapy Pad 22. The ability to control the temperature of the Therapy Pad 22, either reusable or disposable, may increase the pad's effectiveness as a wound dressing. Disposable materials may include less resilient versions of reusable materials and/or completely different materials. In some embodiments, disposable materials may include apertured, breathable, elastomeric and/or embossed films, as well as nonwoven laminates. Wraps may alternatively be configured to be washable, such as by a laundry machine, and therefore may be sanitarily reused.

Figure 8:
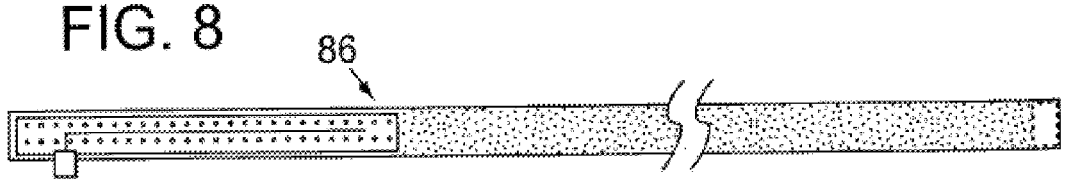
FIG. 8 is a plan view of a contrast therapy pad in accordance with an embodiment of the present invention.

The Thermal Exchange Bladder 68 may be sized and shaped according to a particular range of applications. For example, a 6 inch by 18 inch bladder (as shown at 22 in FIG. 5) may be useful in treating backs, legs, arms, shoulders, and other therapy sites. Although the versatile configuration of Therapy Pad 22 may be used for virtually any therapy site, other Therapy Pads 22 may be configured to even better accommodate particular therapy sites. For example, a 2 inch by 18 inch Bladder 86, as shown in FIG. 8, may be particularly useful for treating smaller therapy sites, such as hands, wrists, feet, ankles, etc. Similarly, a shoulder Therapy Pad 22 may be designed to intimately engage a shoulder therapy site, thus providing comfortable and improved treatment. A jaw Therapy Pad 22, which is useful in treating the facial area, may be designed to comfortably wrap around a head, while positioning a bladder in contact with at least one side of a jaw. It should be understood that the above Therapy Pads are provided as examples, and other Therapy Pads may also be used. Furthermore, each Therapy Pad 22 may include a suitable Elastic Wrap 70 and/or other fastening mechanism.

The therapy system may be used to treat a wide range of conditions, including injured muscles, bones, joints, tendons, ligaments etc. Furthermore, other conditions may be treated, such as mastitis, breasts that are sore from menstruation, and headaches. The therapy system may also be used as a preventative remedy, for example the therapy system may be used during child birth to help alleviate discomfort during labor as well as help minimize resulting soreness and/or discomfort. For example, providing a cold treatment to a recipient's back during child birth may help cool the recipient, thus alleviating immediate discomfort, as well as subsequent soreness.

V. Automated Contrast Therapy Module

Figure 9A:
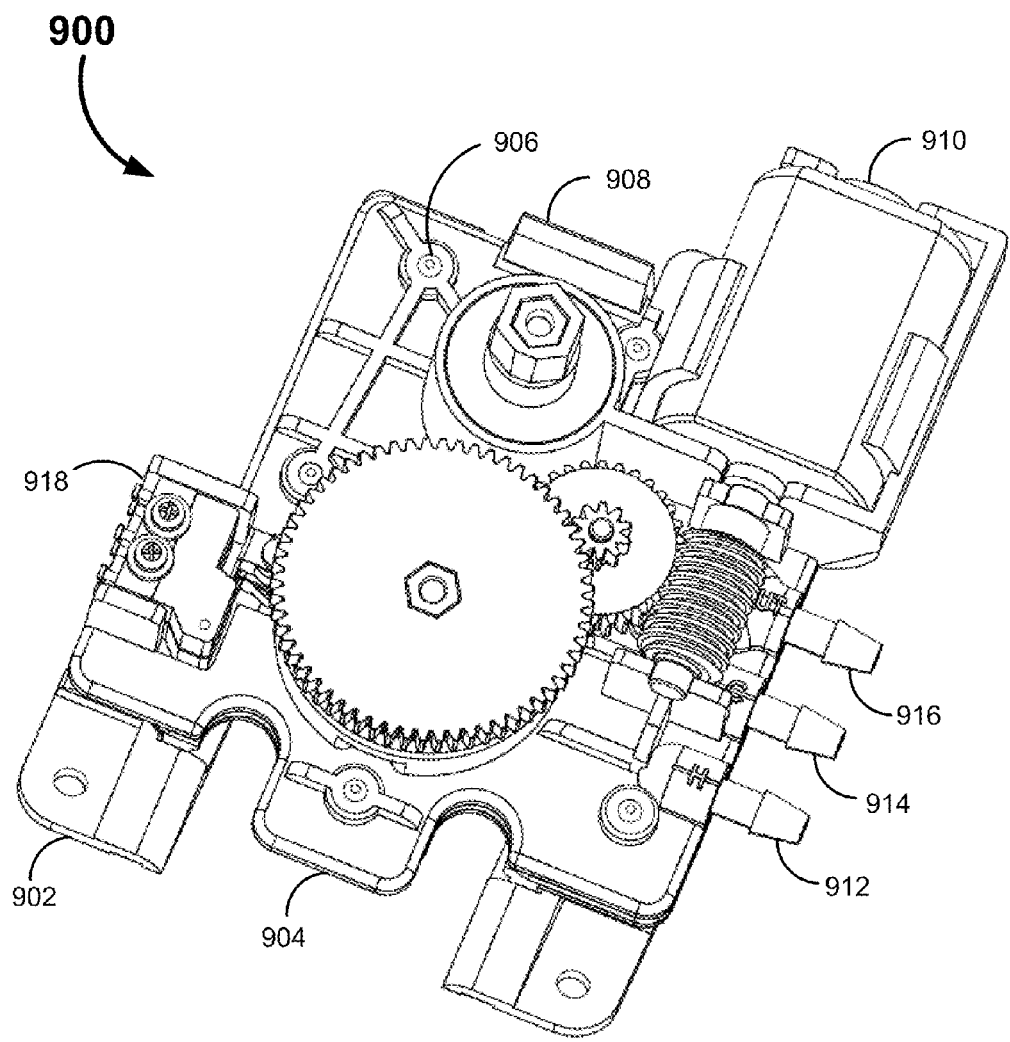
FIG. 9A is an exemplary top view of one embodiment of an automated contrast therapy module with mounting bracket in accordance with the present invention.

FIG. 9A is an exemplary top view of one embodiment of the Automated Contrast Therapy Module 900. The Automated Contrast Therapy Module 900 may be designed to fit within the Pump Unit of the Contrast Therapy System 10. The Automated Contrast Therapy Module 900 may replace the Mixing Valve 16, as seen in FIG. 2B. The Automated Contrast Therapy Module 900 includes a Mounting Bracket 902 which may be designed to couple to the Automated Contrast Therapy Module 900 as well as the pressure module 1300. In some alternate embodiments, the Mounting Bracket 902 may be configured to only engage the Automated Contrast Therapy Case 904. The coupling of the Mounting Bracket 902 to the Automated Contrast Therapy Case 904 may utilize a Mounting Clip 908, screws, adhesives or any other suitable securing mechanism. The Mounting Clip 908 may be configured to release the Automated Contrast Therapy Case 904 to enable ready swapping of the Automated Contrast Therapy Module 900 with the pressure module 1300 or any other functionality module.

The Automated Contrast Therapy Case 904 may be metal, ceramic, polymer or any other suitable material. Ideally, the Automated Contrast Therapy Case 904 may be pressure molded with precision in order to maintain a leak free seal. Additionally, the material utilized for the Automated Contrast Therapy Case 904 may be suitable for long term use at temperatures ranging from the cold reservoir to the hot reservoir. The Automated Contrast Therapy Case 904 may include a single piece, or may include more than one piece as performance and manufacturing needs dictate. When the Automated Contrast Therapy Case 904 includes more than one component, one or more Screws 906 many be utilized to hold the Automated Contrast Therapy Case 904 together. In some embodiments, adhesives, welding, snaps, or other suitable medium may be utilized to hold the components of the Automated Contrast Therapy Case 904 together. As seen on the illustration of FIG. 9A, ribbing, or other structural reinforcement, may be included within the Automated Contrast Therapy Case 904. Such bracing may be necessary to ensure shape and fidelity of the Automated Contrast Therapy Case 904 since the Automated Contrast Therapy Case 904 may be under considerable fluid pressure.

Integrated into the Automated Contrast Therapy Case 904 may be a fluid pathway. The pathway may terminate at the Therapy Fluid Outlet 916 and originate from one or more of the Hot Fluid Inlet 912 and Cold Fluid Inlet 914. Fluid from the cold reservoir may enter the Automated Contrast Therapy Module 900 at the Cold Fluid Inlet 914, whereas fluid from the hot reservoir may enter the Automated Contrast Therapy Module 900 at the Hot Fluid Inlet 912.

A Motor 910 may actuate the automated mixing valve 1014 of the Automated Contrast Therapy Module 900. One or more Switches 918 may sense the position of the automated mixing valve 1014 that is driven by the Motor 910. Feedback from the Switches 918 may be utilized in driving the Motor 910.

Figure 9B:
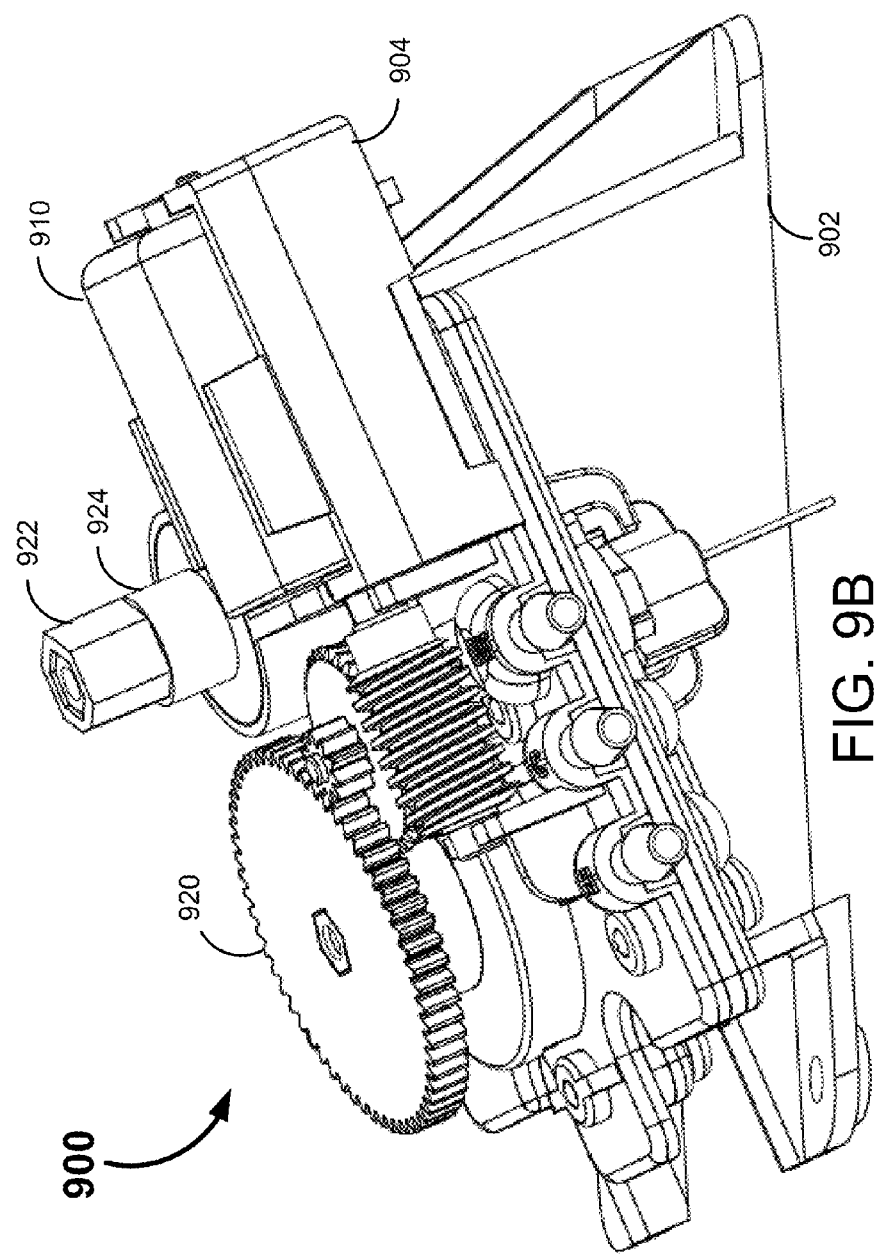
FIG. 9B is an exemplary side view of one embodiment of the automated contrast therapy module with mounting bracket in accordance with the present invention.

FIG. 9B is an exemplary side view of the Automated Contrast Therapy Module 900. Here the Mounting Bracket 902 may be more readily seen. The Motor 910 engages a series of gears which ultimately drives the rotation of an Automated Valve Gear 920. The Automated Valve Gear 920 may then control the position of the automated mixing valve 1014.

The Automated Contrast Therapy Module 900 may also include a Manual Mixing Valve 924 to enable manual control over the fluid temperature. A Manual Valve Nut 922 may engage the Manual Mixing Valve 924 and couple the Manual Mixing Valve 924 with the control dial on the exterior of the lid of the contrast therapy system.

Figure 10A:
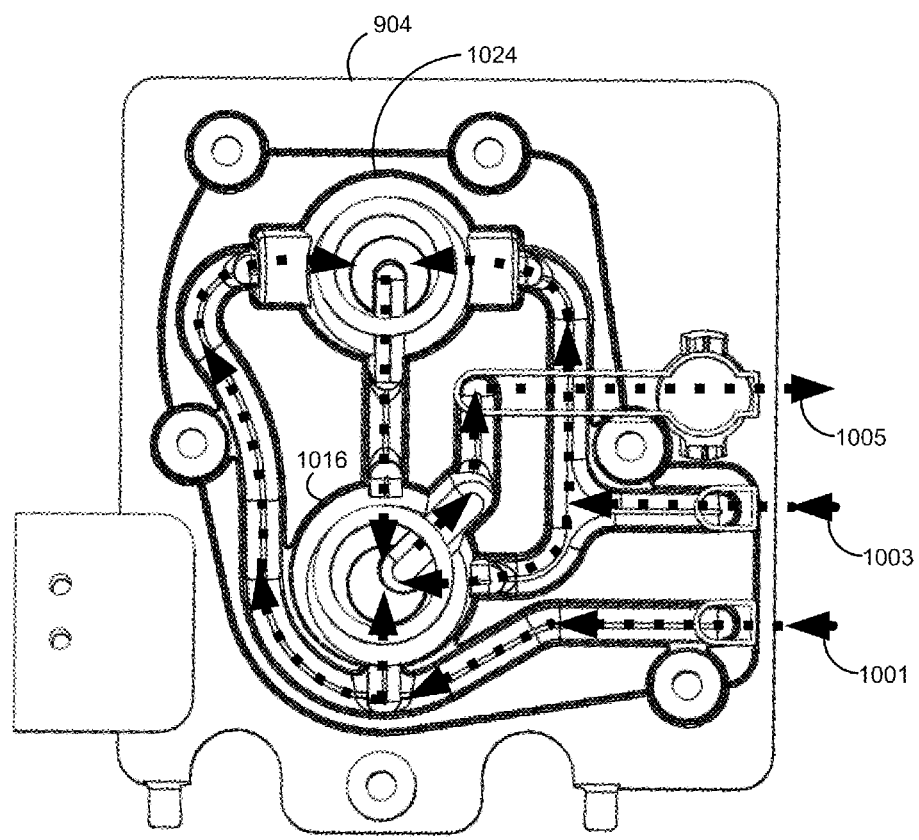
FIG. 10A is an exemplary cut away view of the casing, showing the fluid pathway, of one embodiment of the automated contrast therapy module.

FIG. 10A is an exemplary cut away view of the Automated Contrast Therapy Case 904 showing the fluid pathway. Hot therapy fluid enters the Automated Contrast Therapy Case 904 along the Hot Fluid Pathway 1001. The hot fluid may enter the Automated Mixing Chamber 1016 or the Manual Mixing Chamber 1024. Likewise, cold therapy fluid enters the Automated Contrast Therapy Case 904 along the Cold Fluid Pathway 1003, and may travel to the Automated Mixing Chamber 1016 or the Manual Mixing Chamber 1024. Hot or cold fluid may enter the Manual Mixing Chamber 1024 depending upon the position of the Manual Mixing Valve 924. Fluid mixed within the Manual Mixing Chamber 1024 may travel to the Automated Mixing Chamber 1016. The combination of hot, cold and mixed fluid may enter the Automated Mixing Chamber 1016 at a ratio dictated by the automated mixing valve. In some embodiments, only hot or only cold fluid may enter the automated mixing valve. In some embodiments, a ratio of hot and cold fluid may enter the Automated Mixing Chamber 1016 when the Automated Contrast Therapy Module 900 is automatically mixing the therapy fluid; alternatively, only mixed fluid from the Manual Mixing Chamber 1024 may enter the Automated Mixing Chamber 1016 when the therapy fluid is being mixed manually. From the Automated Mixing Chamber 1016, the final therapy fluid mixture may exit along the Therapy Fluid Pathway 1005.

A dial, or other control mechanism, may be utilized to turn the position of the Manual Mixing Valve 924. A programmable interface may be utilized to select the contrast therapy program which drives the Motor 910. Thus, a myriad of contrast therapy regimes may be provided with relative ease on the part of the therapy recipient or physician.

Figure 10B:
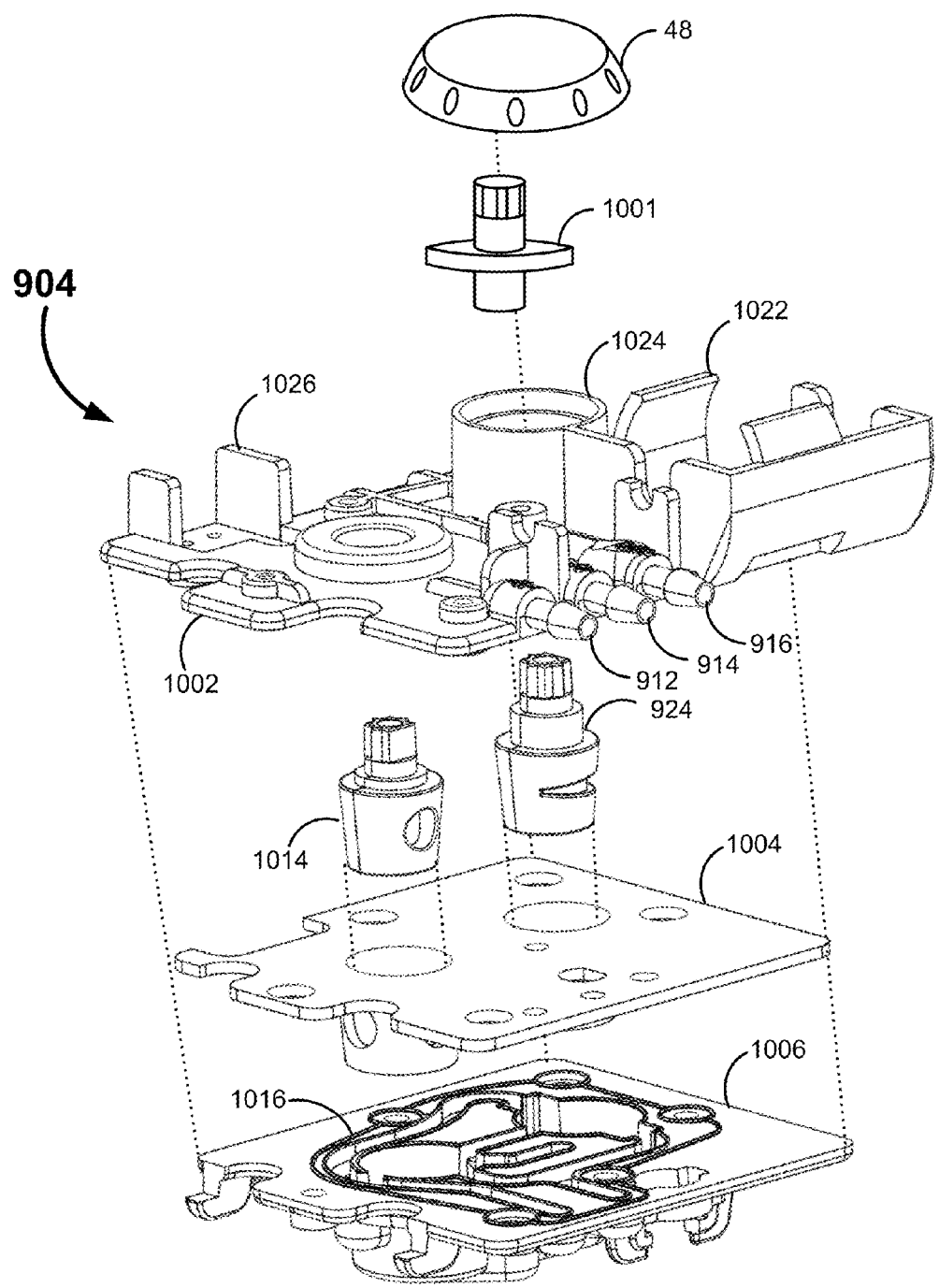
FIG. 10B is an exemplary exploded side view of the casing of one embodiment of the automated contrast therapy module.

FIG. 10B is an exemplary exploded side view of the Automated Contrast Therapy Case 904. Here the Automated Contrast Therapy Case 904 includes two parts, a Top Contrast Therapy Case 1002 and a Bottom Contrast Therapy Case 1006. A Contrast Therapy Casing Seal 1004 may seal the Top Contrast Therapy Case 1002 and Bottom Contrast Therapy Case 1006 together in such a way as to prevent fluid leaking. Dotted lines indicate the arrangement that the shown components are assembled. The Contrast Therapy Casing Seal 1004 may include a rubber, plastic, ceramic or other suitable material. As previously noted, in some embodiments, the Automated Contrast Therapy Case 904 may include a single unit or more components.

On the Top Contrast Therapy Case 1002 a Switch Holder 1026 may be formed to engage the Switches 918, and Motor Holder 1022 may engage the Motor 910. The Automated Mixing Valve 1014 and Manual Mixing Valve 924 engage the Automated Mixing Chamber 1016 and Manual Mixing Chamber 1024, respectively. The Contrast Therapy Casing Seal 1004 may be formed to create a seal around the Automated Mixing Valve 1014 and Manual Mixing Valve 924. Holes and spacing cut in the Contrast Therapy Casing Seal 1004 may enable fluids to circulate along the fluid path. The top of the Automated Mixing Valve 1014 and Manual Mixing Valve 924 may protrude from the top of the Top Contrast Therapy Case 1002 to engage the actuators.

A Valve Adapter 1001 may couple to the Manual Mixing Valve 924. The Valve Adapter 1001 may then couple to the Dial 48. The Valve Adapter 1001 and Dial 48 may be omitted from many of the figures to avoid unnecessary cluttering of the images.

Figure 10C:
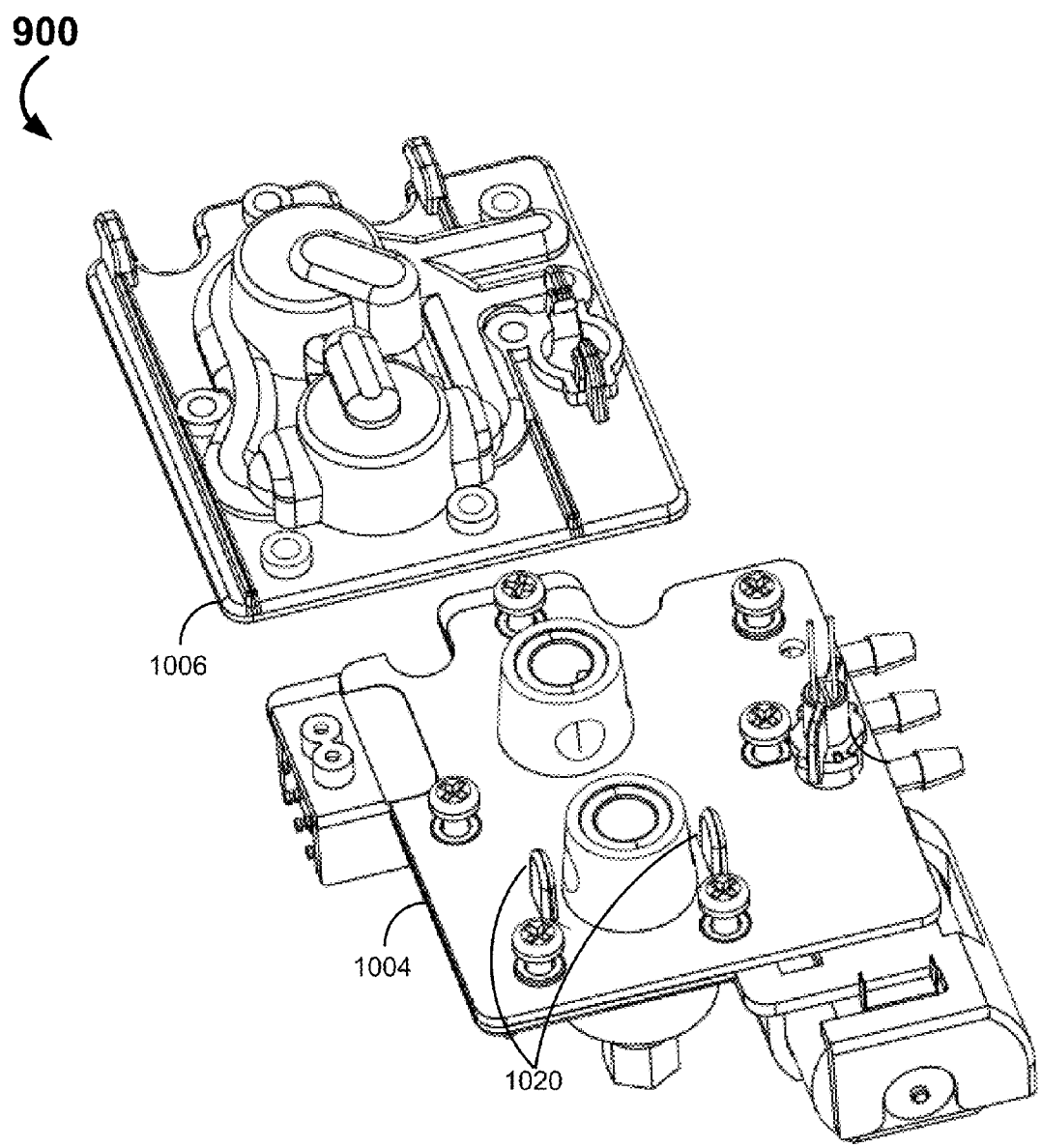
FIG. 10C is an exemplary exploded bottom view of the casing of one embodiment of the automated contrast therapy module.

FIG. 10C is an exemplary exploded bottom view of the Automated Contrast Therapy Case 904. Here the Bottom Contrast Therapy Case 1006 and the Contrast Therapy Casing Seal 1004 may be seen. Two Check Valve Flaps 1020 may also be seen. The Check Valve Flaps 1020 function to keep the hot and cold fluid from traveling through the manual valve to the automated valve when automated valve is in use.

Figure 11A:
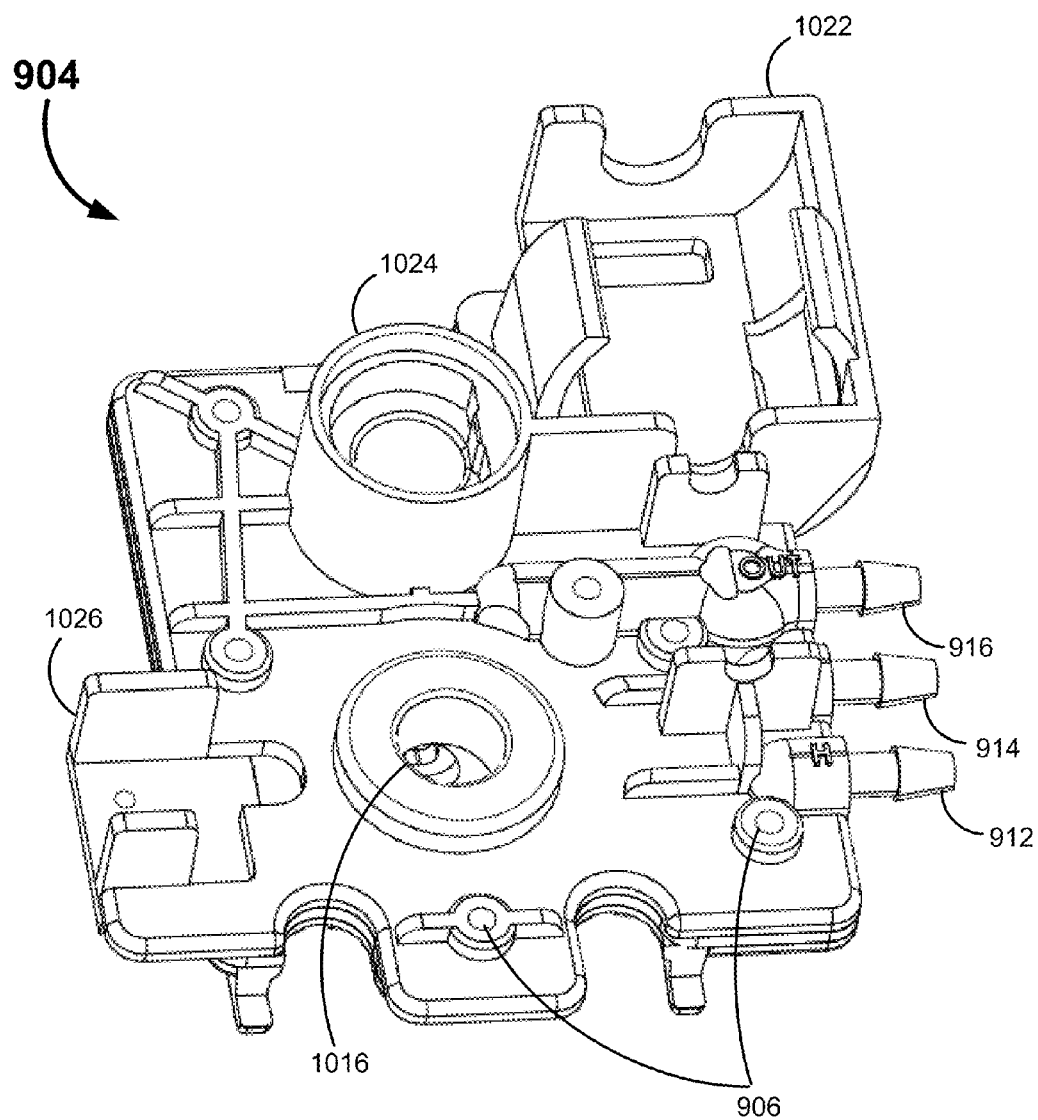
FIG. 11A is an exemplary isometric top view of the casing of one embodiment of the automated contrast therapy module.

FIG. 11A is an exemplary isometric top view of the Automated Contrast Therapy Case 904. Again the Switch Holder 1026 and Motor Holder 1022 may be seen. The Manual Mixing Chamber 1024 and Automated Mixing Chamber 1016 may likewise be seen. In this embodiment, Screws 906 are used to hold the Top Contrast Therapy Case 1002, Contrast Therapy Casing Seal 1004 and Bottom Contrast Therapy Case 1006 together. Fluid is inputted through the Hot Fluid Inlet 912 and Cold Fluid Inlet 914, and the final mixed therapy fluid may be outputted through the Therapy Fluid Outlet 916.

Figure 11B:
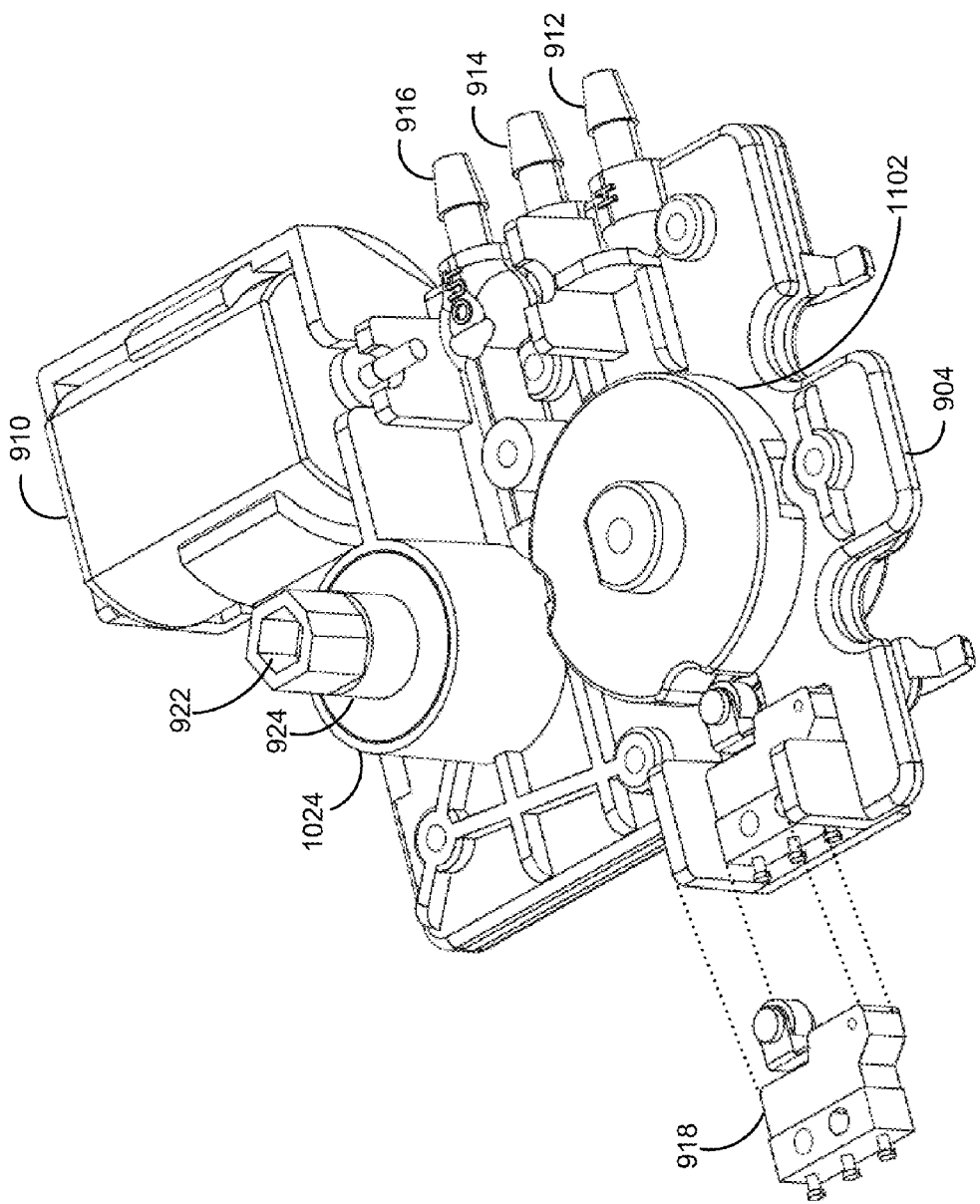
FIG. 11B is an exemplary isometric cutaway top view of one embodiment of the automated contrast therapy module.

FIG. 11B is an exemplary isometric cutaway top view of one embodiment of the automated contrast therapy module. Here the Automated Contrast Therapy Case 904 may be seen with the Motor 910 and Switches 918 in place. Additionally the Manual Mixing Valve 924 and Automated Mixing Valve 1014 are included in the Automated Contrast Therapy Case 904 (the Automated Mixing Valve 1014 is obscured). The Manual Mixing Valve 924 engages a Manual Valve Nut 922, which in turn may engage a dial or other suitable manual actuator. A Positional Dial 1102 engages the Automated Mixing Valve 1014. The Positional Dial 1102 includes grooves along its perimeter. These grooves engage the switching arms of the Switches 918 thereby indicating the position of the Positional Dial 1102 and Automated Mixing Valve 1014. It should be noted that additional systems for determining Automated Mixing Valve 1014 position are contemplated by the present invention. For example, a variable resistor, contact gradient or other suitable mechanism for determining position may be readily employed by the present invention.

Figure 11C:
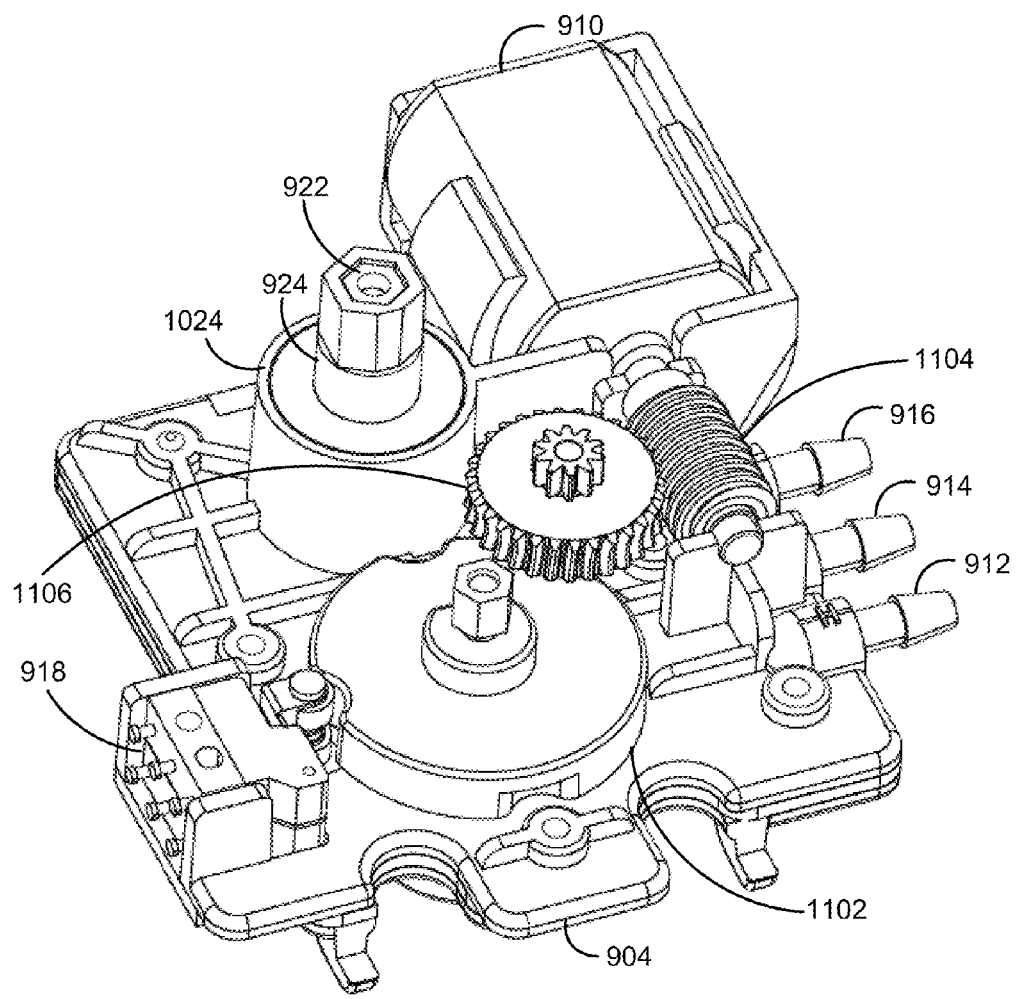
FIG. 11C is an exemplary isometric top view of one embodiment of the automated contrast therapy module.

FIG. 11C is an exemplary isometric top view of one embodiment of the automated contrast therapy module. In this illustration, the Switches 918 are engaging the Positional Dial 1102. Here the Motor 910 may be seen engaging a Screw Gear 1104. As the Motor 910 rotates the Screw Gear 1104, the helical threads of the Screw Gear 1104 engage the teeth of the Intermediate Gear 1106, resulting in it turning.

Figure 11D:
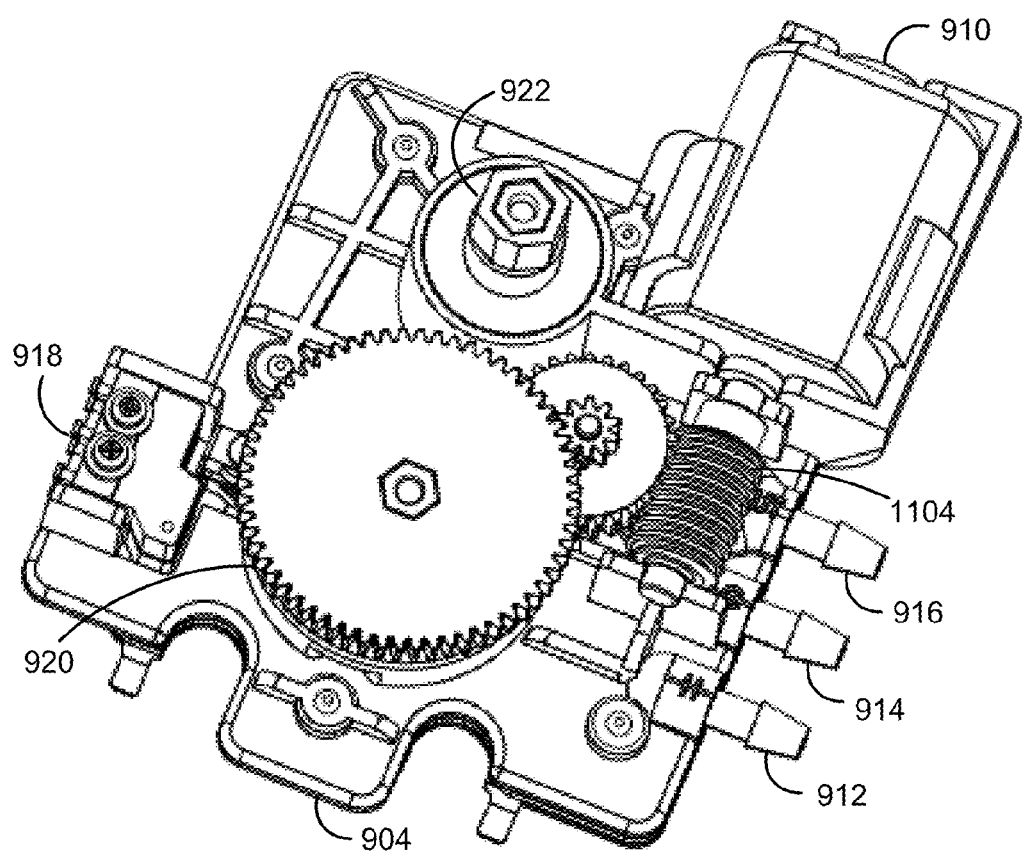
FIG. 11D is an exemplary top view of one embodiment of the automated contrast therapy module.

FIG. 11D is an exemplary top view of one embodiment of the automated contrast therapy module. Here the Automated Valve Gear 920 may be seen coupled to the Positional Dial 1102. Teeth from the Automated Valve Gear 920 engage the geared down teeth of the Intermediate Gear 1106. Thus, as the Motor 910 runs, it turns the Screw Gear 1104. The Screw Gear 1104 turns the Intermediate Gear 1106 and in turn moves the Automated Valve Gear 920. The Automated Valve Gear 920 drives the Positional Dial 1102 and Automated Mixing Valve 1014, thereby controlling fluid flow.

It should be noted that alternate methods of controlling Automated Mixing Valve 1014 position are contemplated by the present invention. For example, belts may replace the gears. More or fewer gears may, additionally, be utilized. In some embodiments, a stepper motor, piston solenoid or other actuator may replace the Motor 910. Additionally, in some embodiments, the Motor 910 may directly engage the Automated Mixing Valve 1014 without intermediate gearing.

Figure 11E:
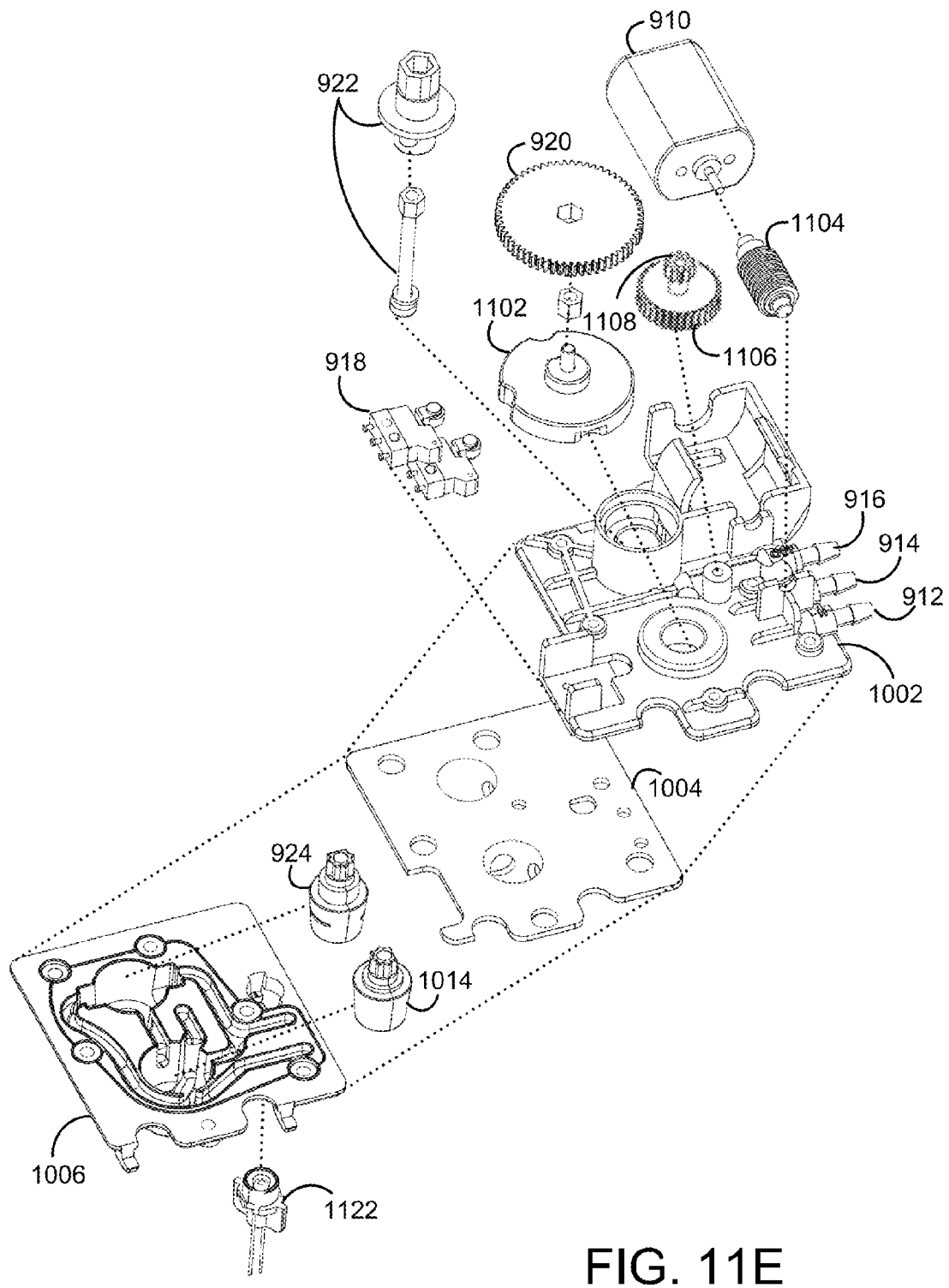
FIG. 11E is an exemplary exploded isometric top view of one embodiment of the automated contrast therapy module.

FIG. 11E is an exemplary exploded isometric top view of one embodiment of the automated contrast therapy module. Again, the dashed lines indicate relative position of the components when assembled. A Thermocouple 1122 engages the Bottom Contrast Therapy Case 1006 at the Therapy Fluid Outlet 916. The Thermocouple 1122 collects data on fluid therapy temperature. This data may be utilized to aid in automated mixing control, and may additionally act as a safety mechanism. Alternatively, mixing times may be controlled by a timer, and the thermocouple data may merely be displayed to the user. Therapy fluid that is too hot, or too cold, may trigger a shutdown of the system to prevent discomfort and possible tissue damage. This thermocouple 1122 data may also be used in conjunction with a digital display to output temperature of the therapy fluid to the user.

The Manual Mixing Valve 924 and Automated Mixing Valve 1014 may engage the Bottom Contrast Therapy Case 1006. A Contrast Therapy Casing Seal 1004 sandwiched between the Bottom Contrast Therapy Case 1006 and Top Contrast Therapy Case 1002 thereby enabling a leak free fluid pathway. An automated actuation system engages the Top Contrast Therapy Case 1002 to control position of the Automated Mixing Valve 1014. This actuation system includes the Motor 910 coupled to the Screw Gear 1104, which in turn engages the Intermediate Gear 1106. The Intermediate Gear 1106 includes an up-gearing 1108 which then engages the Automated Valve Gear 920. The Automated Valve Gear 920 couples to the Positional Dial 1102, which finally engages the Automated Mixing Valve 1014. The Switches 918 couple to the Top Contrast Therapy Case 1002 and sense the position of the Positional Dial 1102.

The Manual Mixing Valve 924 couples to the Manual Valve Nut 922, which in turn may couple to the dial or other control on the exterior of the lid of the contrast therapy system.

Figure 12A:
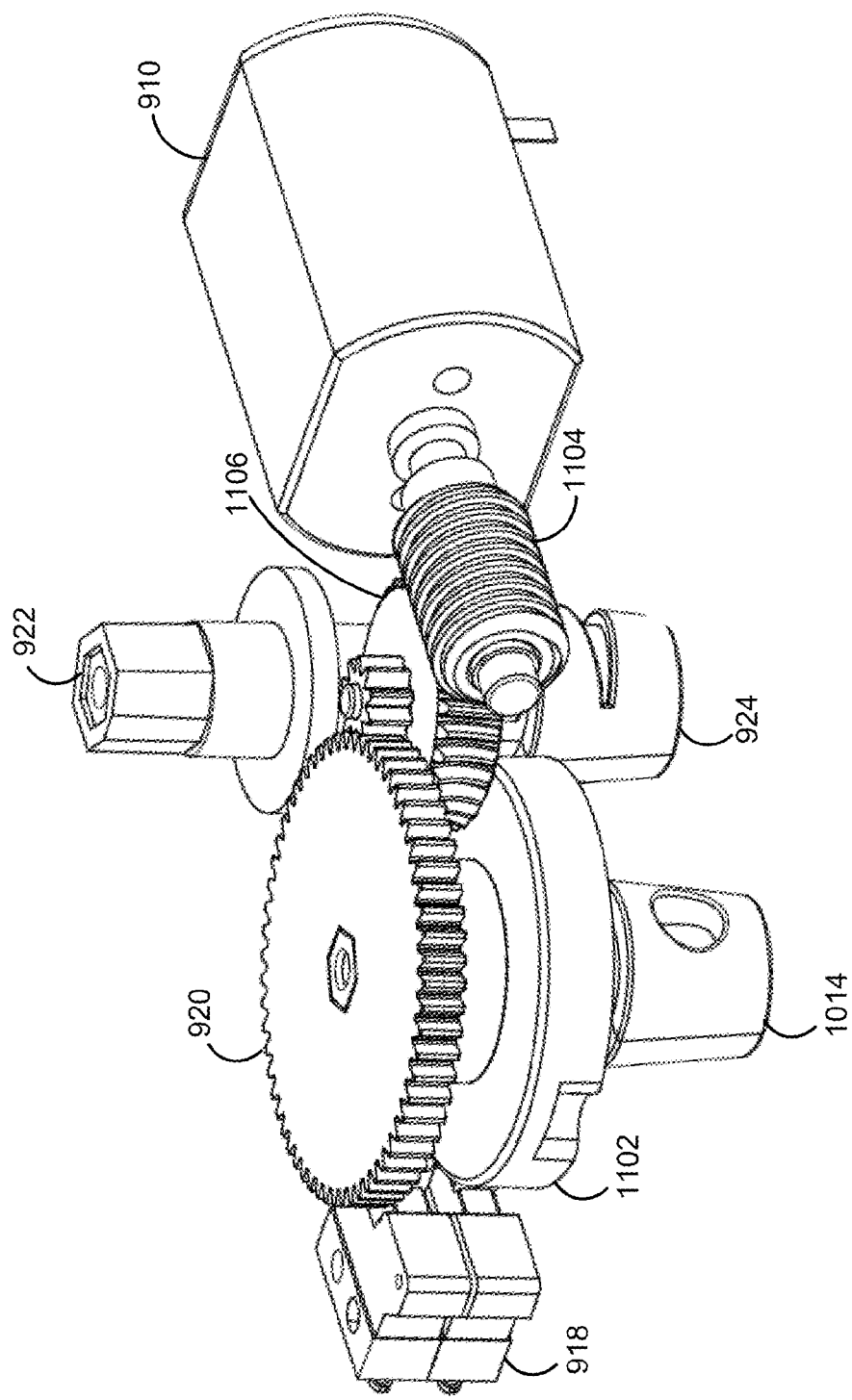
FIG. 12A is an exemplary isometric side view of the valve actuation system of one embodiment of the automated contrast therapy module.
Figure 12B:
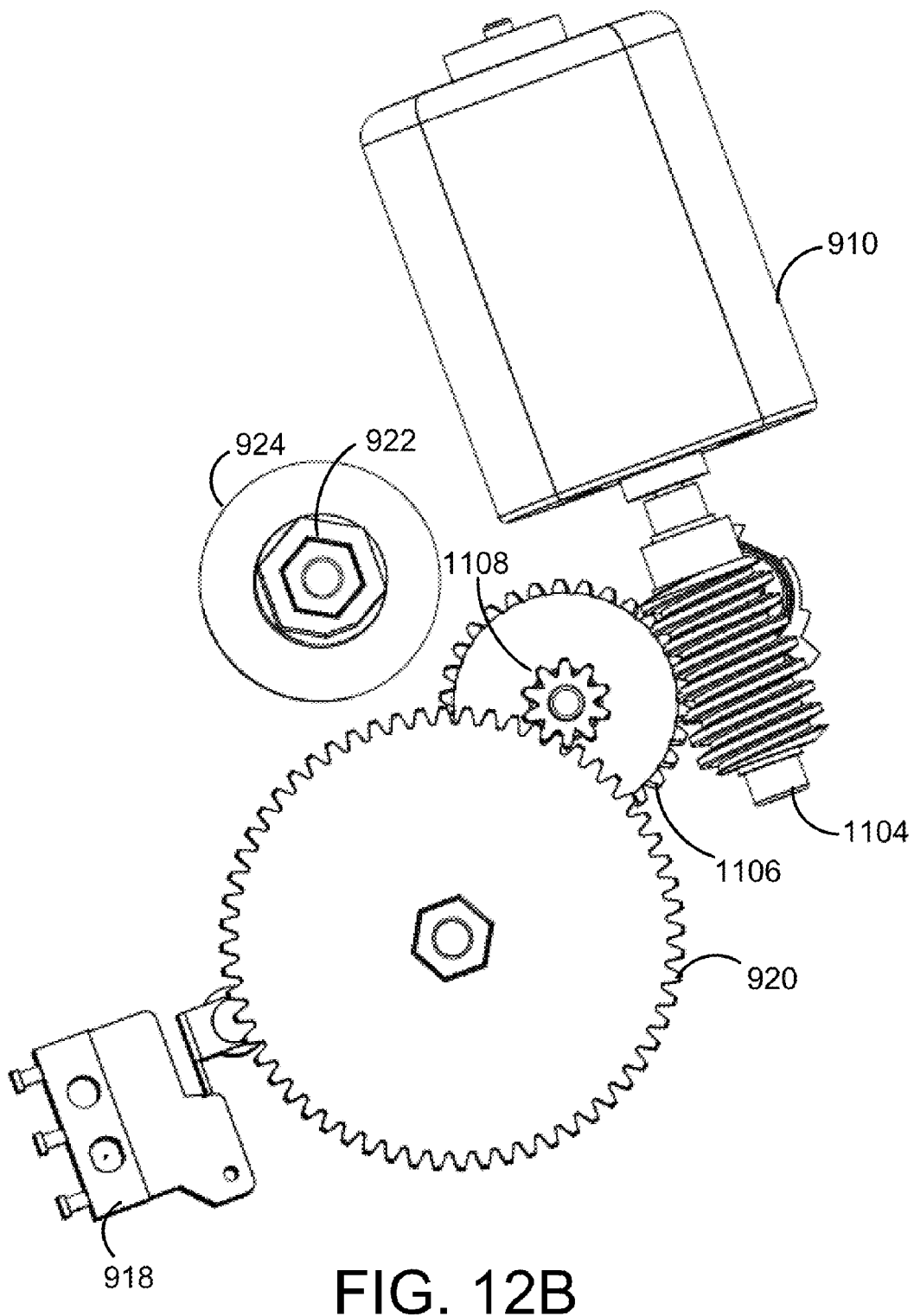
FIG. 12B is an exemplary top view of the valve actuation system of one embodiment of the automated contrast therapy module.
Figure 12C:
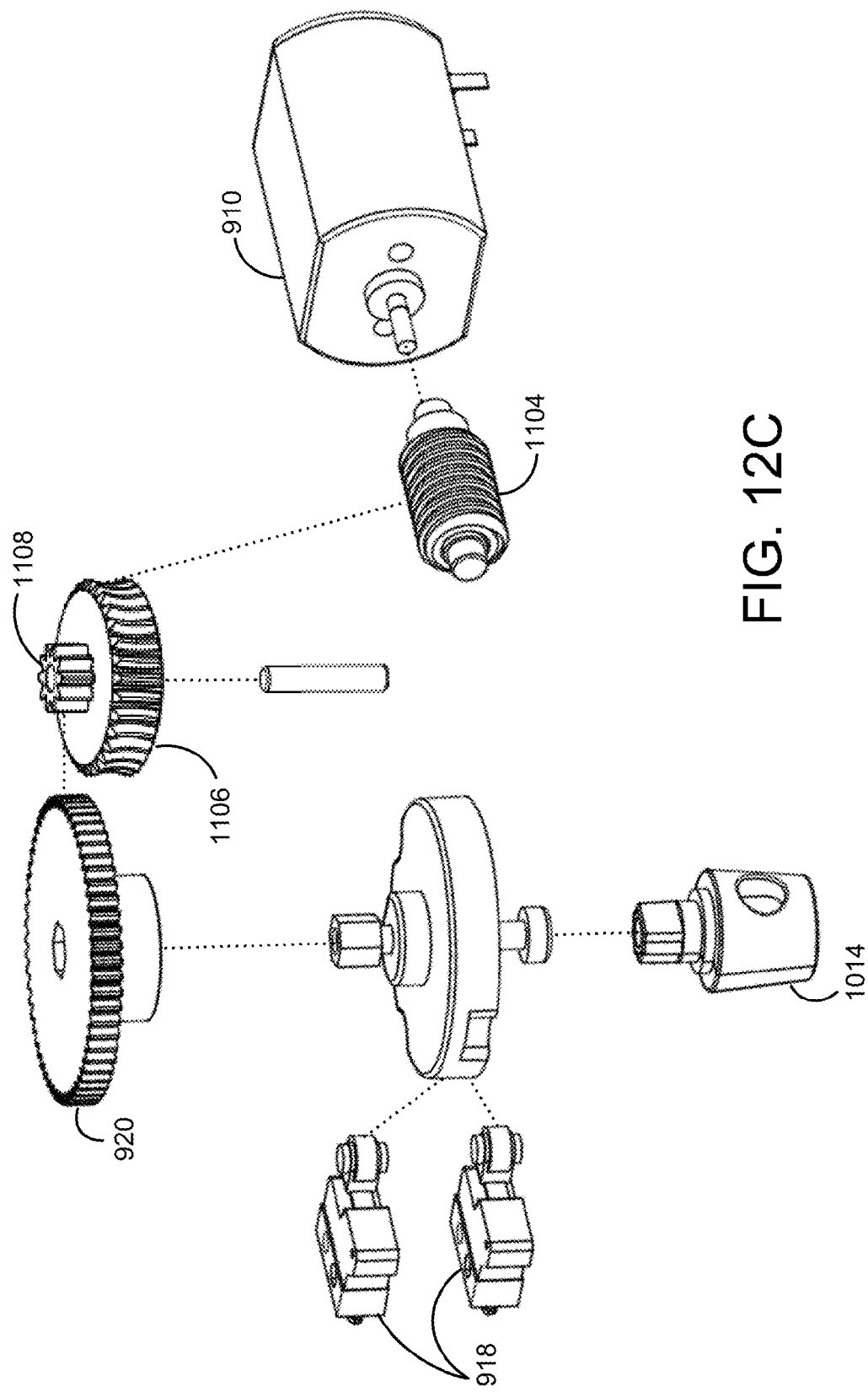
FIG. 12C is an exemplary exploded isometric side view of the valve actuation system of one embodiment of the automated contrast therapy module.

FIGS. 12A to 12C are exemplary views of the valve actuation system. As previously noted, this actuation system includes the Motor 910 coupled to the Screw Gear 1104, which in turn engages the Intermediate Gear 1106. The Intermediate Gear 1106 includes a coupled up-gearing 1108 which then engages the Automated Valve Gear 920. The Automated Valve Gear 920 couples to the Positional Dial 1102, which finally engages the Automated Mixing Valve 1014. The Switches 918 couple to the Top Contrast Therapy Case 1002 and sense the position of the Positional Dial 1102.

VI. Automated Pressure Therapy Module

Figure 13A:
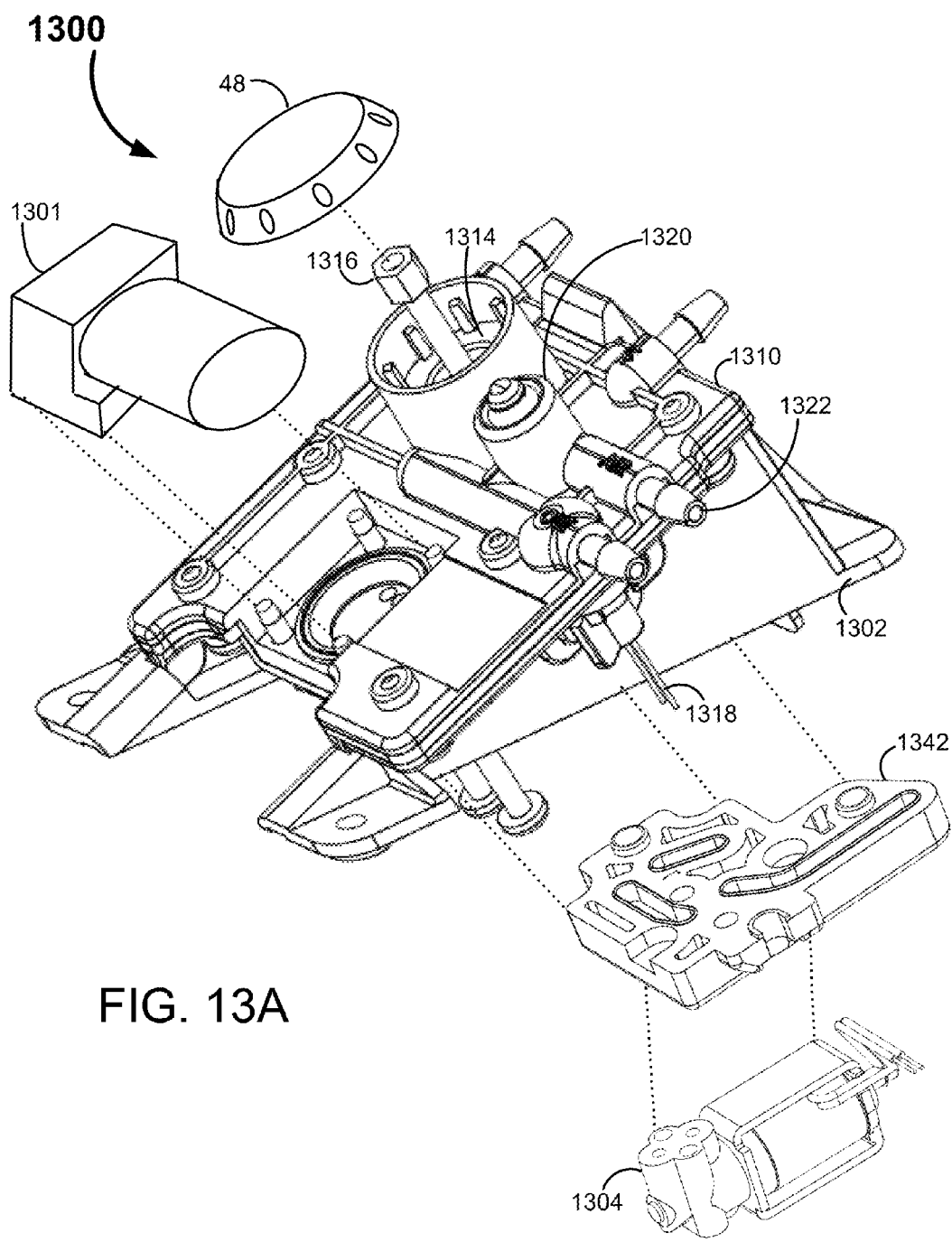
FIG. 13A is an exemplary side view of one embodiment of the automated pressure therapy module with mounting bracket in accordance with the present invention.
Figure 13B:
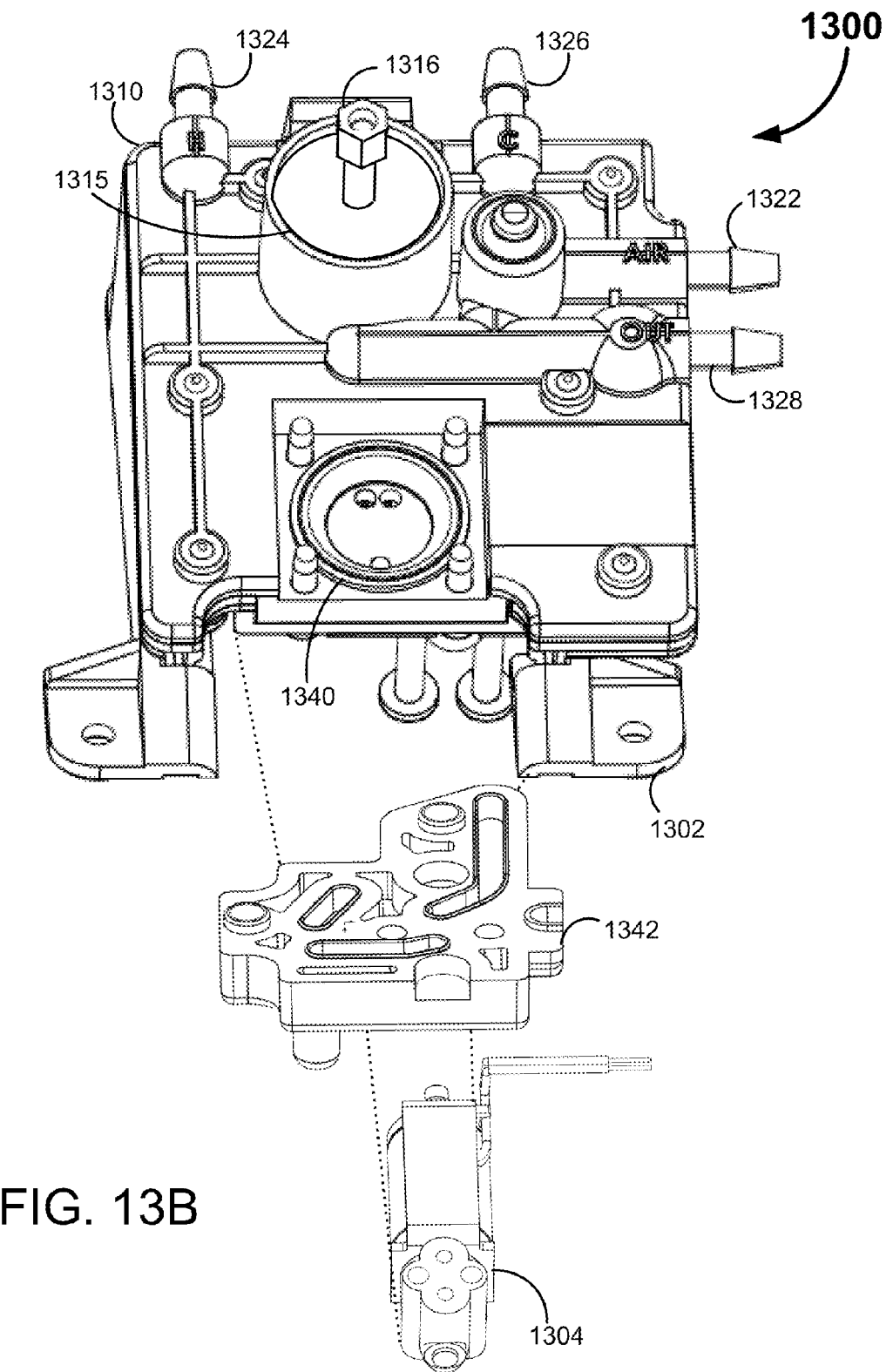
FIG. 13B is an exemplary isometric top view of one embodiment of the automated pressure therapy module with mounting bracket in accordance with the present invention.

FIGS. 13A and 13B are exemplary side views of one embodiment of the Compression Therapy Module 1300. The Compression Therapy Module 1300 may also be referred to as a pressure therapy module. Such a system may enable manual contrast therapy fluid circuit with an integrated pressure control for inflation of a compression bladder. This enables the contrast therapy system to provide compression therapy with thermal therapy.

Like the Automated Contrast Therapy Module 900, the Compression Therapy Module 1300 may include a Mounting Bracket 1302. The Compression Therapy Module 1300 and Automated Contrast Therapy Module 900 may be of similar dimensions thereby enabling the modules to be interchangeably integrated within a contrast therapy system. This enables reduced manufacturing costs, reduced unit weight and possible configurability of systems as is needed.

The Compression Therapy Module 1300 may include a Mounting Bracket 1302 which may be designed to couple to the Compression Therapy Case 1310 as well as the Automated Contrast Therapy Module 900. In some alternate embodiments, the Mounting Bracket 1302 may be configured to only engage the Compression Therapy Case 1310. The coupling of the Compression Therapy Case 1310 to the Mounting Bracket 1302 may utilize a bracket clip, screws, adhesives or any other suitable securing mechanism. The Mounting Bracket 1302 may be configured to release the Compression Therapy Case 1310 to enable ready swapping of the Compression Therapy Module 1300 with the Automated Contrast Therapy Module 900 or any other functionality module.

The Compression Therapy Case 1310 may be metal, ceramic, polymer or any other suitable material. Ideally, the Compression Therapy Case 1310 may be pressure molded with precision in order to maintain a leak free seal. Additionally, the material utilized for the Compression Therapy Case 1310 may be suitable for long term use at temperatures ranging from the cold reservoir to the hot reservoir. The Compression Therapy Case 1310 may include a single piece, or may include more than one piece as performance and manufacturing needs dictate. When the Compression Therapy Case 1310 includes more than one component, one or more screws many be utilized to hold the Compression Therapy Case 1310 together. In some embodiments, adhesives, welding, snaps, or other suitable medium may be utilized to hold the components of the Compression Therapy Case 1310 together. Coupled to the Compression Therapy Case 1310 may be a Solenoid Mount 1342. A Pneumatic Solenoid 1304 may in turn couple to the Solenoid Mount 1342. An Air Pump 1301 may couple to the Compression Therapy Case 1310 and provide pressurized air.

As seen on the illustration of FIG. 13B, ribbing, or other structural reinforcement, may be included within the Compression Therapy Case 1310. Such bracing may be necessary to ensure shape and fidelity of the Compression Therapy Case 1310 since the Compression Therapy Case 1310 may be under considerable fluid and air pressure.

Integrated into the Compression Therapy Case 1310 may be a fluid pathway as well as an air pathway. The fluid pathway may terminate at the Therapy Fluid Outlet 1328 and originate from one or more of the Hot Fluid Inlet 1324 and Cold Fluid Inlet 1326. Fluid from the cold reservoir may enter the Compression Therapy Module 1300 at the Cold Fluid Inlet 1326, whereas fluid from the hot reservoir may enter the Compression Therapy Module 1300 at the Hot Fluid Inlet 1324.

An Air Pump 1301 may be mounted on the Compression Therapy Case 1310 at a Pump Mounting Site 1340. The Air Pump 1301 may provide pressurized air for the compression therapy. Pressurized air may travel to the Solenoid Mount 1342. A Pneumatic Solenoid 1304 may in turn couple to the Solenoid Mount 1342, controlling the pressure of the outputted air. The pressurized air may exit the Compression Therapy Case 1310 via the Pressurized Air Outlet 1322 and may then travel to a splitter. From the splitter the pressurized air may travel to a compression bladder of the therapy wrap and may enter the pressure switch (not illustrated). Pressurized air may travel through rubber or rigid tubing (not shown). The pressure switch may include a pressure sensor in order to provide feedback and control of the compression therapy. Additionally, the pressure switch may be configured to vent the pressurized air when the pressure gets too high. This is a safety mechanism to prevent over compression, discomfort for the wearer and even injury.

Feedback from the pressure switch and the controls on the contrast therapy Pump Unit may be received by the Pneumatic Solenoid 1304. The Pneumatic Solenoid 1304 may then provide control over the output air pressure. In some embodiments, the Pneumatic Solenoid 1304 may be configured to rapidly change output pressures, thereby creating a massage-like, or vibrating, compression therapy. The Pneumatic Solenoid 1304 may include a "slow bleed" valve which acts to slowly release pressure over time. This feature provides a failsafe mechanism in case the Compression Therapy Module 1300 becomes unresponsive, or the power to the contrast therapy system is terminated. Additionally, a mechanical Pressure relief valve 1320 may be incorporated into the Compression Therapy Case 1310 to provide a final safety measure. Thus, if at any point the pressure exceeds a safe operable level, the seal of the Pressure relief valve 1320 may burst, thereby preventing over inflation of the compression bladder and possible patient injury.

A Mixing Valve Nut 1316 and Mixing Valve 1314 may be included in the Compression Therapy Case 1310 to enable manual contrast therapy control. A Dial 48 may then couple to the mixing nut for user control of the mixing ratio. In FIG. 13B, the Mixing Valve 1314 is obscured by the Valve Adapter 1315.

Figure 14A:
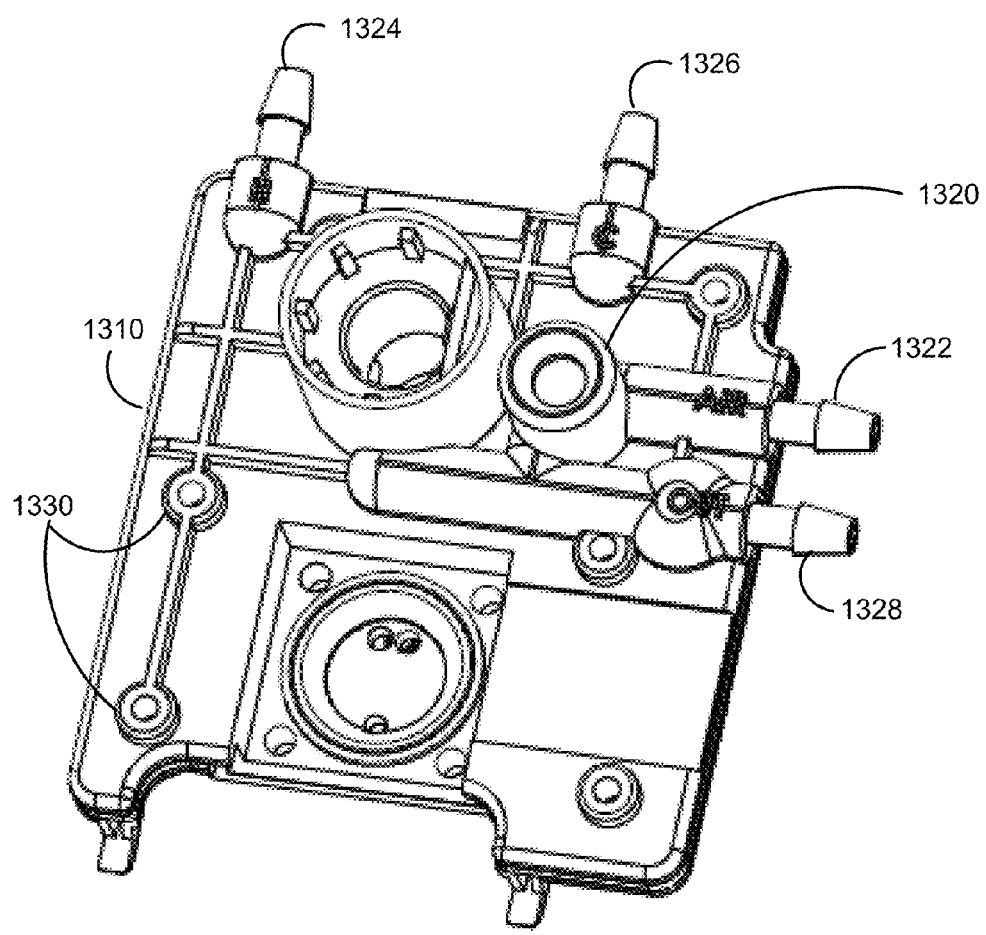
FIG. 14A is an exemplary isometric top view of the casing of one embodiment of the automated pressure therapy module.
Figure 14B:
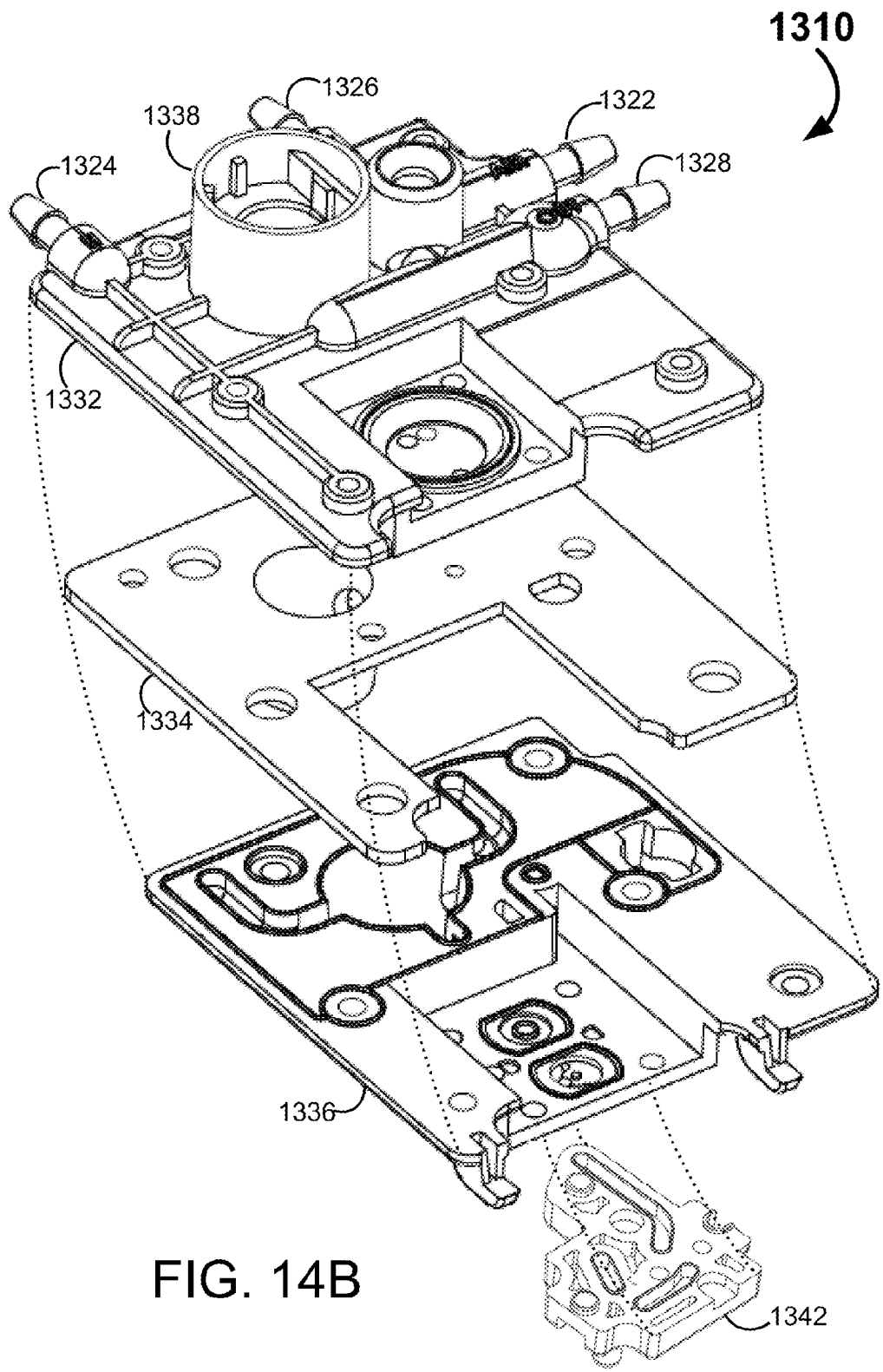
FIG. 14B is an exemplary exploded isometric view of the casing of one embodiment of the automated pressure therapy module.

FIGS. 14A and 14B are views of the Compression Therapy Case 1310 of the Compression Therapy Module 1300. The Screws 1330 may be readily seen in these illustrations. Additionally, the fluid pathway may likewise be seen. The hot fluid pathway extends from the Hot Fluid Inlet 1324 along the Top Compression Therapy Case 1332. Then the fluid extends down to the Mixing Chamber 1338 where the Mixing Valve 1314 is located. Likewise the cold fluid path immediately extends down into the Bottom Compression Therapy Case 1336 and to the Mixing Chamber 1338. The output channel travels through the Top Compression Therapy Case 1332 to the Therapy Fluid Outlet 1328. Between the Top Compression Therapy Case 1332 and Bottom Compression Therapy Case 1336 is a Compression Casing Seal 1334 to prevent fluid or air from leaking. The Compression Casing Seal 1334 may include a rubber, plastic, ceramic or other suitable material. As previously noted, in some embodiments, the Compression Therapy Case 1310 may include a single unit or more components.

Figure 14C:
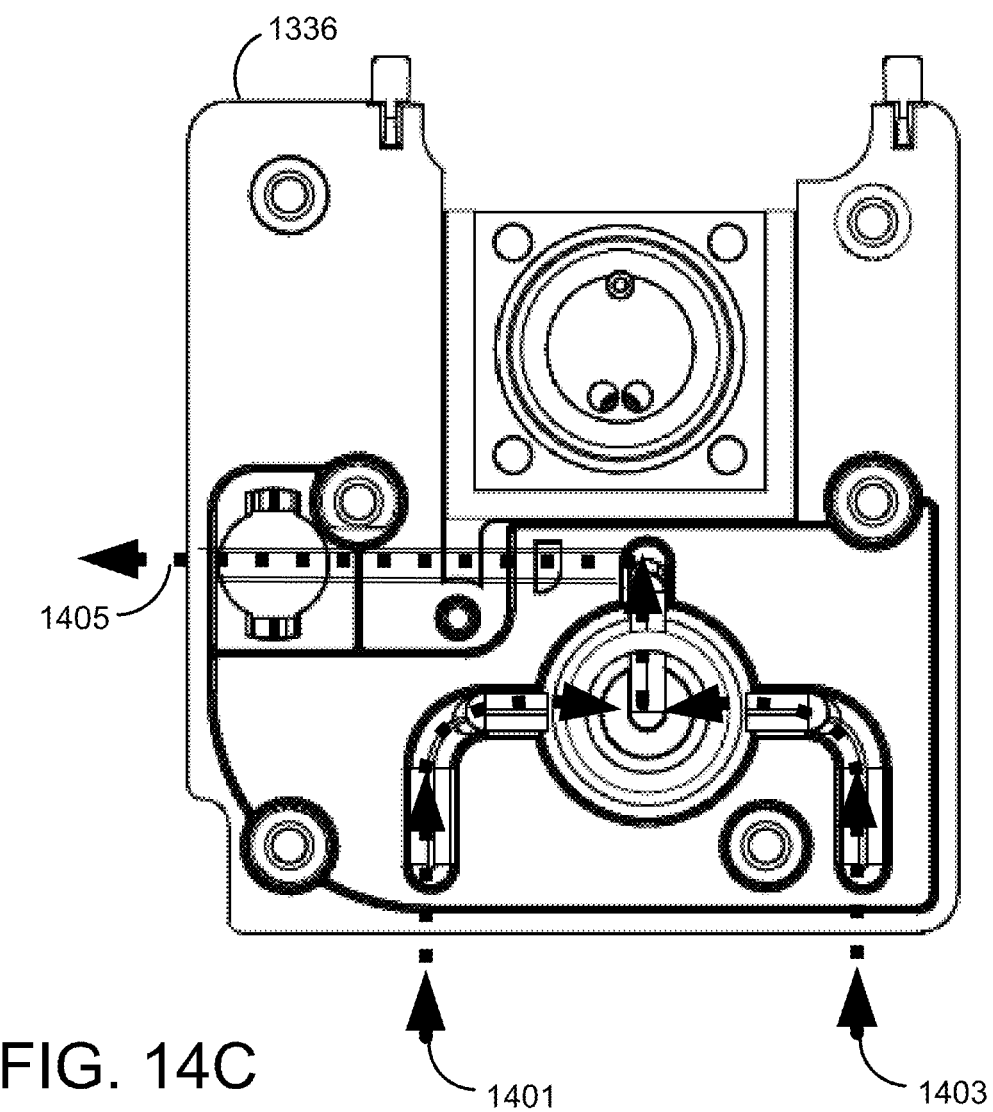
FIG. 14C is an exemplary cut away view of the casing, showing the fluid pathway, of one embodiment of the automated pressure therapy module.

FIG. 14C is an exemplary cut away view of the Bottom Compression Therapy Case 1336 showing the fluid pathway. Hot therapy fluid enters the Bottom Compression Therapy Case 1336 along the Hot Fluid Pathway 1401. The hot fluid may enter the mixing chamber. Likewise, cold therapy fluid enters the Bottom Compression Therapy Case 1336 along the Cold Fluid Pathway 1403, and may travel to the mixing chamber.

Hot or cold fluid may enter the mixing chamber depending upon the position of the Mixing Valve 1314. A dial, or other control mechanism, may be utilized to turn the position of the Mixing Valve 1314. The final therapy fluid may then be output via the Therapy Fluid Path 1405.

Figure 15:
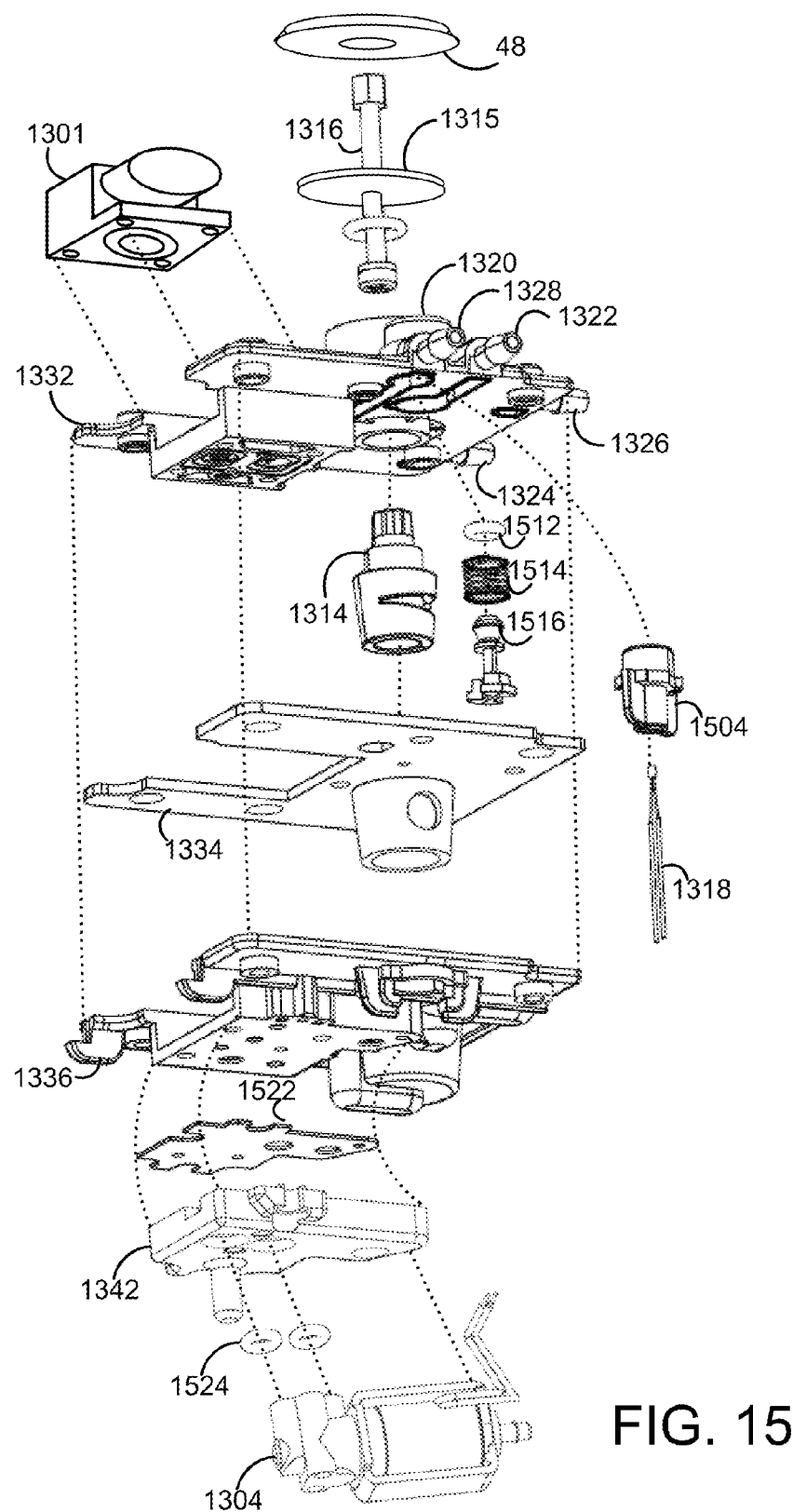
FIG. 15 is an exemplary exploded isometric bottom view of one embodiment of the automated pressure therapy module.

FIG. 15 is an exemplary exploded isometric bottom view of one embodiment of the automated pressure therapy module. Here the Pneumatic Solenoid 1304 may be seen coupling to the Solenoid Mount 1342, which in turn couples to the Bottom Compression Therapy Case 1336. An Air Seal 1522 prevents air from leaking at this junction. The Air Seal 1522 may be rubber, plastic or other suitable material. Likewise, Air O-rings 1524 may seal the junction between the Pneumatic Solenoid 1304 and the Solenoid Mount 1342.

Likewise a Thermocouple 1318 may engage a Thermocouple Holder 1504 and couple to the Bottom Compression Therapy Case 1336. The Thermocouple 1318 may sense the temperature of the outgoing therapy fluid and thereby provide feedback for regulating therapy temperature or for display on the contrast therapy lid.

The Bottom Compression Therapy Case 1336 couples to the Compression Casing Seal 1334 and the Top Compression Therapy Case 1332. A Mixing Valve 1314 may be located within the Compression Therapy Case 1310 formed by the Top Compression Therapy Case 1332, Compression Casing Seal 1334 and Bottom Compression Therapy Case 1336.

The Pressure relief valve 1320 may include a valve with a Piston 1516, a Piston Spring 1514 and an O-ring 1512. The Spring 1514 may hold the Piston 1516 and O-ring 1512 against the Top Compression Therapy Case 1332. If pressure becomes too large, however, the spring may bias, thereby opening the Pressure relief valve 1320.

An Air Pump 1301 may be mounted on the Top Compression Therapy Case 1332. The air pump may pressurize air and supply the pressurized air to the Pneumatic Solenoid 1304. The Pneumatic Solenoid 1304 may then regulate the pressurized air into the Top Compression Therapy Case 1332 which is then outputted via the Pressurized Air Outlet 1322. A Pressure relief valve 1320 may be incorporated into the Top Compression Therapy Case 1332 to prevent excessive pressures.

The Mixing Valve Nut 1316 may couple to the Mixing Valve 1314 and a control mechanism, such as a dial, in the contrast therapy lid.

Figure 16:
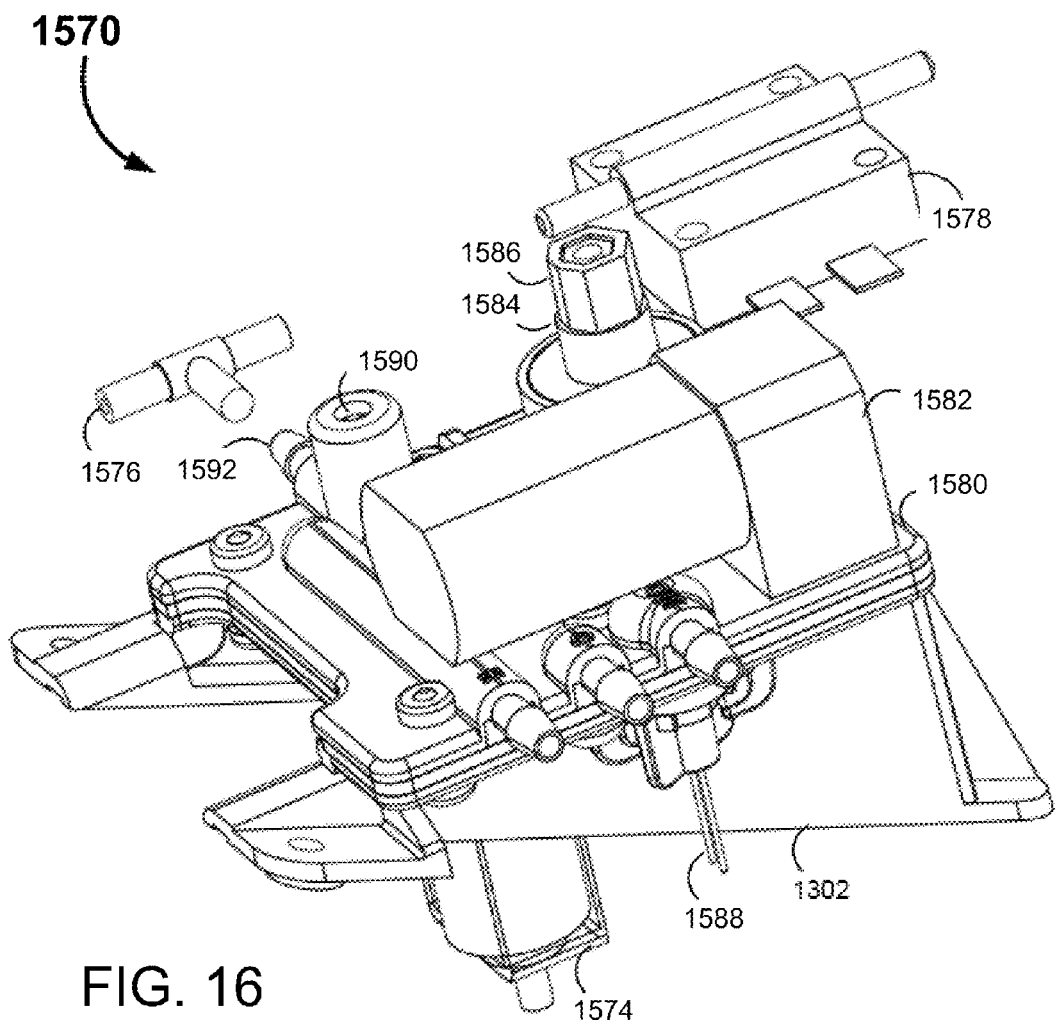
FIG. 16 is an exemplary side view of another embodiment of an automated pressure therapy module.

FIG. 16 is an exemplary side view of another embodiment of an Alternate Compression Therapy Module 1570. Like the above embodiment, such a system may enable manual contrast therapy fluid circuit with an integrated pressure control for inflation of a compression bladder. This enables the contrast therapy system to provide compression therapy with thermal therapy.

Like the Automated Contrast Therapy Module 900, the Alternate Compression Therapy Module 1570 may include a Mounting Bracket 1302. The Alternate Compression Therapy Module 1570 and Automated Contrast Therapy Module 900 may be of similar dimensions thereby enabling the modules to be interchangeably integrated within a contrast therapy system. This enables reduced manufacturing costs, reduced unit weight and possible configurability of systems as is needed.

Integrated into the Compression Therapy Case 1580 may be a fluid pathway as well as an air pathway. The fluid pathway may terminate at the Therapy Fluid Outlet and originate from one or more of the Hot Fluid Inlet and Cold Fluid Inlet. Fluid from the cold reservoir may enter the Compression Therapy Module 1570 at the Cold Fluid Inlet, whereas fluid from the hot reservoir may enter the Compression Therapy Module 1570 at the Hot Fluid Inlet.

An Air Pump 1582 may be mounted on the Compression Therapy Case 1580. The Air Pump 1582 may provide pressurized air for the compression therapy. The pressurized air may exit the Compression Therapy Case 1580 via the Pressurized Air Outlet 1592 and may then travel to a Splitter 1576. From the Splitter 1576 the pressurized air may travel to a compression bladder of the therapy wrap and may enter the Pressure Switch 1578. Pressurized air may travel through rubber or rigid tubing (not shown). The Pressure Switch 1578 may include a pressure sensor in order to provide feedback and control of the compression therapy. Additionally, the Pressure Switch 1578 may be configured to vent the pressurized air when the pressure gets too high. This is a safety mechanism to prevent over compression, discomfort for the wearer and even injury.

Feedback from the Pressure Switch 1578 and the controls on the contrast therapy lid may be received by a Pneumatic Solenoid 1574. The Pneumatic Solenoid 1304 may then provide control over the output air pressure. In some embodiments, the Pneumatic Solenoid 1574 may be configured to rapidly change output pressures, thereby creating a massage-like, or vibrating, compression therapy. The Pneumatic Solenoid 1304 may include a "slow bleed" valve which acts to slowly release pressure over time. This feature provides a failsafe mechanism in case the Compression Therapy Module 1300 becomes unresponsive, or the power to the contrast therapy system is terminated. Additionally, a mechanical Safety Blowout 1590 may be incorporated into the Compression Therapy Case 1580 to provide a final safety measure. Thus, if at any point the pressure exceeds a safe operable level, the seal of the Safety Blowout 1590 may burst, thereby preventing over inflation of the compression bladder and possible patient injury.

A Mixing Valve Nut 1586 and Mixing Valve 1584 may be included in the Compression Therapy Case 1580 to enable manual contrast therapy control.

VII. Method of Administering Contrast Thermal Therapy

FIG. 17 shows, generally at 1600, a method of administering contrast therapy to a therapy recipient. Method 1600 includes, at 1602, providing a volume of a relatively hot fluid. As explained above, a fluid may be received by a hot reservoir, where it may be heated by a heater. The relatively hot fluid may be virtually any temperature, with temperatures of approximately 100 to 105 degrees Fahrenheit being suitable for many applications. The method further includes, at 1604, providing a volume of a relatively cold fluid. Fluid may be received by a cold reservoir, where it may be cooled. In some embodiments, ice slurry is used to cool fluid passing through the cold reservoir, and in some embodiments a cooler is used. The cold fluid may be virtually any temperature (cooler than the hot fluid), with temperatures of approximately 32 to 45 degrees Fahrenheit being suitable for many applications.

At 1606, the method includes selecting relative amounts of the hot and cold fluids to mix as a therapy fluid with a desired initial therapy temperature. A mixture of hot and cold fluids with a specific ratio may be selected with a mixing valve, or similar mechanism, that is configured to receive the hot and cold fluids, and pass the mixture of the hot and cold fluids as a therapy fluid. The ratio of hot to cold fluid in the therapy fluid may range from 100% hot fluid to 100% cold fluid, as well as any intermediate ratio. The temperature of the therapy fluid corresponds to the ratio of hot and cold fluids mixed, with greater percentages of hot fluid resulting in higher temperatures, and greater percentages of cold fluid resulting in cooler temperatures. The therapy fluid's maximum temperature is approximately the temperature of the hot fluid, and is achieved by selecting a ratio of all hot fluid and no cold fluid. Similarly, the therapy fluid's minimum temperature is approximately the temperature of the cold fluid, and is achieved by selecting a ratio of all cold fluid and no hot fluid.

As shown at 1608, the method further includes circulating the therapy fluid with the initial therapy temperature through a Therapy Pad 22. The therapy fluid may be circulated in a pulsing stream, so as to impart a vibration that is useful in providing a therapeutic massage. Of course, the flow may instead be smooth. At 1610, the method includes applying the Therapy Pad 22 to the therapy recipient. The temperature of the therapy fluid may be translated through the Therapy Pad 22 to the therapy recipient. For example, if the initial temperature of the therapy fluid is relatively hot, for instance 105 degrees Fahrenheit, the Therapy Pad may be used to heat a therapy site on the therapy recipient. Similarly, a therapy fluid with a relatively cold therapy temperature, such as 40 degrees Fahrenheit, may be used to cool a therapy site.

The method further includes, at 1610, returning the therapy fluid to at least one of the volume of hot fluid and the volume of cold fluid. Returning the therapy fluid to either or both of the volumes of hot and cold fluids allows the therapy fluid to be recycled. The returned therapy fluid may then be heated and/or cooled, and eventually may be recalculated to the Therapy Pad 22. In this manner, a limited volume of fluid in a system may be used to provide an ongoing therapy. The fluid may be repeatedly heated and/or cooled, and thus the character of the treatment may be continually changed.

As shown at 1612, the method may also include selecting relative amounts of the hot and cold fluids to mix as a therapy fluid with a desired contrast therapy temperature different than the initial therapy temperature. By changing the relative amounts of hot and cold fluids, the resulting temperature of the therapy fluid may be changed, which changes the therapy received by the therapy recipient. It is within the scope of the invention to make such temperature changes quickly, such as in under a minute, which may result in an average temperature change greater than 1 degree Fahrenheit per second. At 1614, the method may further include circulating the therapy fluid with the contrast therapy temperature through the Therapy Pad 22. Circulating the therapy fluid with the contrast therapy temperature allows the therapy recipient to experience a cold treatment immediately after a hot treatment or a hot treatment immediately after a cold treatment. It should be understood that the period of change between respective treatments is ideally very small, such as less than one minute. This process may be repeated one or more times, and each time the relative amounts of hot and cold fluids may be selected to result in a desired therapy temperature.

The present invention can also be practiced with other techniques for providing thermal or contrast therapy to a therapy recipient. For example, it is possible, using the therapy pad of the instant invention, to be configured to incorporate massage pads for massage therapy at the therapy site as well.

Additionally, it should be noted that due to the particular vascular activity of swelling and particular injuries, contrast therapy may be undesired and instead a constant temperature may be preferred. For example, when dealing with head pain, migraine pain is due to vasodilatation, thus a cold therapy may be beneficial for the migraine sufferer to dull pain and cause the capillaries to constrict, thereby eliminating the pain source. Likewise, since in traditional compression and tension headaches there is vasoconstriction, heat therapy may aid by dilating the capillaries and relieving constriction.

In sum, the present invention provides an automated contrast therapy module and a pressure therapy module. These functionality modules enable contrast therapy systems to be built which are lighter in weight, cheaper and which include more functionality than previous systems.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. An automated thermal contrast therapy module for a contrast therapy system, the automated contrast therapy module comprising:

a casing configured to include a fluid pathway, wherein the casing includes at least one of a cold fluid inlet, a hot fluid inlet and a therapy fluid outlet;

a manual mixing valve configured to mix a ratio of a cold fluid and a hot fluid to generate a manually mixed therapy fluid, wherein the manual mixing valve is part of the fluid pathway;

an automated mixing valve configured to mix a ratio of the cold fluid and the hot fluid and the manually mixed therapy fluid to generate a final therapy fluid, wherein the automated mixing valve is part of the fluid pathway;

an interface configured to enable selecting of a mode of mixing, wherein the mode of mixing includes at least one of manual mixing, automatic mixing and at least one contrast therapy programs; and an automated mixing valve actuator configured to control the automated mixing valve, wherein the automated mixing valve actuator is driven in response to at least one of an elapse time and the selected mode of mixing.

2. The automated contrast therapy module of claim 1, wherein the automated contrast therapy module is removable from the contrast therapy system.

3. The automated contrast therapy module of claim 1, wherein the automated mixing valve actuator comprises:
   a motor configured to rotate a screw gear;
      at least one gear configured to rotate, wherein the at least one gear is coupled to the screw gear, and wherein the at least one gear rotates in response to rotation of the screw gear;
      a position dial configured to rotate in response to the rotation of the at least one gear, wherein the position dial includes grooves, and wherein rotation of the position dial rotates the automated mixing valve; and
      at least one switch configured to sense the position of the position dial, wherein the switch includes biasing arms, and wherein the biasing arms flex in response to the grooves on the position dial.

4. The automated contrast therapy module of claim 1, wherein the automated contrast therapy module is configured to output at least one of the manually mixed therapy fluid and the final therapy fluid, and wherein the outputted at least one of the manually mixed therapy fluid and the final therapy fluid are provided to a therapy bladder.

5. The automated contrast therapy module of claim 1, wherein the automated contrast therapy module includes a temperature sensor configured to measure the temperature of the final therapy fluid, and wherein the automated mixing valve actuator is driven in response to at least one of the temperature of the final therapy fluid and the selected mode of mixing.

6. A method for providing automated contrast therapy, useful in association with an automated contrast therapy module for a contrast therapy system, the method comprising:
   enabling a user to select a ratio of a colder fluid and a hotter fluid;
   mixing the user selected ratio of colder fluid and hotter fluid to generate a manually mixed therapy fluid;
   enabling the user to select a mode of mixing, wherein the mode of mixing includes at least one of manual mixing, automatic mixing and at least one contrast therapy program;
   mixing a ratio of the cold fluid and the hot fluid and the manually mixed therapy fluid to generate a final therapy fluid in response to the selected mode of mixing; and
   outputting the generated final therapy fluid to a therapy bladder pad of the contrast therapy system.

7. The method of claim 6, further comprising mixing a second ratio of the cold fluid and the hot fluid and the manually mixed therapy fluid to generate a contrast therapy fluid.

8. The method of claim 7, further comprising outputting the generated contrast therapy fluid to the therapy bladder of the contrast therapy system.

9. The method of claim 8, further comprising outputting the contrast therapy fluid and the final therapy fluid in timed intervals.

10. The method of claim 6, further comprising outputting at least one of the manually mixed therapy fluid and the final therapy fluid.

11. The method of claim 6, further comprising outputting measuring the temperature of the final therapy fluid and adjusting the ratio of the cold fluid and the hot fluid and the manually mixed therapy fluid in response to the temperature of the final therapy fluid.

12. A compression therapy module for a contrast therapy system, the compression therapy module comprising:
   a casing configured to include a pressurized air pathway, wherein the casing includes an air outlet;
   an air pump configured to pressurize air, wherein the air pump couples to the casing, and wherein the air pump is part of the air pathway;
   a pneumatic solenoid configured to regulate the pressure of the pressurized air, wherein the pneumatic solenoid is part of the air pathway; and
   a pressure monitor configured to measure the pressure of the pressurized air.

13. The compression therapy module of claim 12, further comprising a pressure relief valve configured to release pressure from the pressurized air when above a threshold pressure.

14. The compression therapy module of claim 12, further comprising:
   the casing further configured to include a fluid pathway, wherein the casing includes at least one of a cold fluid inlet, a hot fluid inlet and a therapy fluid outlet; and
   a mixing valve configured to mix a ratio of a cold fluid and a hot fluid to generate a therapy fluid, wherein the mixing valve is part of the fluid pathway.

15. The compression therapy module of claim 14, wherein the compression therapy module is configured to output the therapy fluid and the pressurized air.

16. The compression therapy module of claim 12, wherein the compression therapy module includes a mounting bracket, and wherein the mounting bracket fits a standard sized volume in the contrast therapy system.

* * * * *